US010093987B2

(12) United States Patent
Oldham-Haltom et al.

(10) Patent No.: US 10,093,987 B2
(45) Date of Patent: *Oct. 9, 2018

(54) MULTIPLEXED KRAS MUTATION DETECTION ASSAY

(71) Applicant: EXACT SCIENCES DEVELOPMENT COMPANY, LLC, Madison, WI (US)

(72) Inventors: Rebecca Oldham-Haltom, Marshall, WI (US); Hatim Allawi, Madison, WI (US); Hongzhi Zou, Middleton, WI (US); Michael J. Domanico, Madison, WI (US); Graham P. Lidgard, Madison, WI (US)

(73) Assignee: EXACT SCIENCES DEVELOPMENT COMPANY, LLC, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/686,065

(22) Filed: Aug. 24, 2017

(65) Prior Publication Data
US 2018/0066319 A1 Mar. 8, 2018

Related U.S. Application Data

(63) Continuation of application No. 14/811,266, filed on Jul. 28, 2015, now Pat. No. 9,783,856, which is a continuation of application No. 13/594,674, filed on Aug. 24, 2012, now Pat. No. 9,127,318.

(60) Provisional application No. 61/548,639, filed on Oct. 18, 2011.

(51) Int. Cl.
C12Q 1/68 (2018.01)
C12Q 1/6886 (2018.01)
C12Q 1/6858 (2018.01)

(52) U.S. Cl.
CPC ......... C12Q 1/6886 (2013.01); C12Q 1/6858 (2013.01); C12Q 2600/156 (2013.01); C12Q 2600/16 (2013.01)

(58) Field of Classification Search
CPC .................................................. C12Q 1/68
See application file for complete search history.

(56) References Cited

U.S. PATENT DOCUMENTS

| 2003/0203382 A1* | 10/2003 | Shuber ................ C12Q 1/6858 435/6.12 |
| 2005/0186588 A1 | 8/2005 | Lyamichev et al. |
| 2006/0147955 A1 | 7/2006 | Allawi et al. |
| 2008/0160524 A1 | 7/2008 | Ma et al. |
| 2009/0253142 A1 | 10/2009 | Allawi et al. |
| 2010/0105575 A1 | 4/2010 | Wang et al. |
| 2011/0136118 A1 | 6/2011 | Kreader et al. |
| 2012/0122105 A1 | 5/2012 | Oldham-Haltom et al. |
| 2012/0122106 A1 | 5/2012 | Zou et al. |

FOREIGN PATENT DOCUMENTS

| JP | 2011019512 | 2/2011 |
| WO | WO2010048691 | 5/2010 |

OTHER PUBLICATIONS

Stratagene (Gene Characterization Kits; 1988).*
Weiner et al. (Kits and their unique role in molecular biology: a brief retrospective, BioTechniques 44:701-704 (25th Anniversary Issue, Apr. 2008)).*
Amicarelli, et al., "FLAG assay as a novel method for real-time signal generation during PCR: application to detection and genotyping of KRAS codon 12 mutations", Nucleic Acids Res., 2007, 35(19): e131.
Ahlquist, et al. "Next-Generation Stool DNA Test Accurately Detects Colorectal Cancer and Large Adenomas", Gastroenterology, 2012;142:248-256.
Ahlquist, et al. "The Stool DNA Test Is More Accurate Than the Plasma Septin 9 Test in Detecting Colorectal Neoplasia", Clinical Gastroenterology and Hepatology, 2012;10:272-277.
Ayogi, et al. "PCR, Molecular Biology Problem Solver: A Laboratory Guide", Chapter 11, pp. 291-329, 2001.
Communication and Extended European Search Report dated May 19, 2015 for European patent application No. 12841997.5, 5 pages.
Di Fiore, et al., "Clinical relevance of KRAS mutation detection in metastatic colorectal cancer treated by Cetuximab plus chemotherapy", Br J Cancer, 2007, 96:1166-9.
Hedman, et al. "Overcoming Inhibition in Real-Time Diagnostic PCR", Methods Mol Biol. 2013;943:17-48.
Heigh, et al. "Detection of Colorectal Serrated Polyps by Stool DNA Testing: Comparison with Fecal Immunochemical Testing for Occult Blood (FIT)", PLOS ONE, 2014, vol. 9, Issue 1, e85659, pp. 1-6.
Hirani, et al., "Sensitive Quantification of Somatic Mutations Using Molecular Inversion Probes", Anal. Chem., 2011, 83 (21), pp. 8215-8221.
Imperiale, et al. "Multitarget Stool DNA Testing for Colorectal-Cancer Screening", The New England Journal of Medicine, 2014, pp. 1-11.
Krypuy, et al."High resolution melting analysis for rapid and sensitive EGFR and KRAS mutation detection in formalin fixed paraffin embedded biopsies", BMC Cancer May 21, 2008;8:142.
Lidgard, et al. "Clinical Performance of an Automated Stool DNA Assay for Detection of Colorectal Neoplasia", Clinical Gastroenterology and Hepatology, 2013;11:1313-1318.
Noutsias, et al. "Preamplification techniques for real-time RT-PCR analyses of endomyocardial biopsies", BMC Mol Biol. 2008; 9: 3.
Oliner, et al., "A comparability study of 5 commercial KRAS tests", Diagn Pathol., 2010, 5:23. doi: 10.1186/1746-1596-5-23.

(Continued)

Primary Examiner — Aaron A Priest
(74) Attorney, Agent, or Firm — James S. Keddie; Bozicevic, Field & Francis LLP

(57) ABSTRACT

Provided herein is reagent mixture comprising multiplexed amplification reagents and flap assay reagents for detecting, in a single reaction, mutant copies of the KRAS gene that contain any of the 34A, 34C, 34T, 35A, 35C, 35T or 38A point mutations. Methods that employ the reagent mix and kits for performing the same are also provided.

12 Claims, 7 Drawing Sheets

Specification includes a Sequence Listing.

(56) References Cited

OTHER PUBLICATIONS

Parsons, et al. "Genotypic selection methods for the direct analysis of point mutations" Mutat Res. Oct. 1997;387 (2)97-121.
Sasaki, et al., "Nras and Kras mutation in Japanese lung cancer patients: Genotyping analysis using LightCycler", Oncol Rep, 2007, 18:623-8.
Sarasqueta, et al., "SNaPshot and StripAssay as valuable alternatives to direct sequencing for KRAS mutation detection in colon cancer routine diagnostics", J Mol Diagn., Mar. 2011;13(2):199-205.
Tadokoro, et al. "Rapid quantification of periodontitis-related bacteria using a novel modification of Invader PLUS technologies", Microbiol Res. 2010;165(1):43-9.
Tadokoro, et al."Quantitation of viral load by real-time PCR-monitoring Invader reaction", J Virol Methods. Feb. 2009;155(2):182-6.
Tsuchihashi, et al. "Progress in high throughput SNP genotyping methods", Pharmacogenomics J. 2002;2(2):103-10.

\* cited by examiner

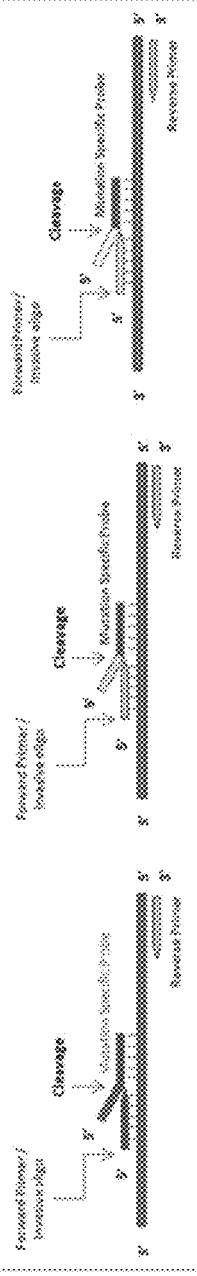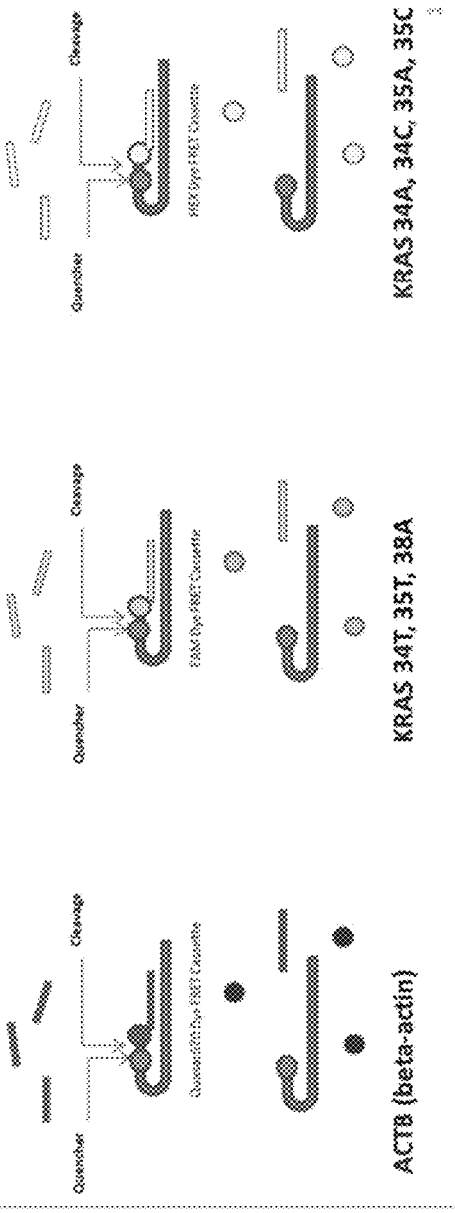
Fig. 3

| Marker | Intercept | Slope |
|---|---|---|
| ACTB | 30.5 | -3.25 |
| KRAS 35C | 29.49 | -3.35 |
| KRAS 38A | 30.93 | -3.32 |

| Table 3. Summary of samples tested and results for 2-dye and 3-dye QuARTS assay configurations | | | | | |
|---|---|---|---|---|---|
| Samples tested in 2- and 3-dye configurations | | Tissue Type | | | |
| | | # of normals | # of adenomas | # of cancers | All (total) |
| Total number | | 19 | 16/15* | 52 | 71 |
| Number of WT | | 19 | 9/8* | 32 | 51 |
| Number of KRAS positive by sequencing | | 0 | 8 | 20 | 28 |
| Number of samples with ≥2.45 percent mutation in KRAS QuARTS assay | 3-dye configuration | 0 | 8 | 20 | 28 |
| | 2-dye configuration | 0 | 8 | 20 | 28 |
| * 1 WT adenoma sample was was tested in 2-dye but not in 3-dye assay due to insufficient volume. | | | | | |

| Table 4. Gap in percent mutation between colorectal normal samples (WT) and KRAS positive cancer and adenoma samples | | | |
|---|---|---|---|
| 86 samples tested in both 2- and 3-dye configurations | Minimum % mutation of sequence positive samples | Maximum % mutation of sequence negative Normals | |
| 2-dye configuration | 8.34 | 0.55 | |
| 3-dye configuration | 12.60 | 0.21 | |

| Table 5. Summary of samples tested and KRAS QuARTS assay results for 191 well-characterized tissue samples | | | | |
|---|---|---|---|---|
| | Tissue Type | | | |
| | # of normals | # of adenomas | # of cancers | All (total) |
| Number per tissue type | 47 | 48 | 96 | 191 |
| Number of WT | 47 | 26 | 59 | 132 |
| Number of KRAS positive by sequencing | 0 | 22 | 37 | 59 |
| Number of samples with ≥2.45 percent mutation in KRAS QuARTS assay | 0 | 22 | 37 | 59 |

| Table 6. Summary of percent mutation by tissue type for 191 tissue samples tested with 3-dye configuration assay | | | | | | |
|---|---|---|---|---|---|---|
| Tissue Type | KRAS mutation samples by sequencing | | | KRAS WT samples by sequencing | | |
| | Minimum percent mutation | Maximum percent mutation | Mean percent mutation | Minimum percent mutation | Maximum percent mutation | Mean percent mutation |
| Adenoma | 6.58% | 129.72% | 42.06 ± 30.89% | 0.01% | 1.08% | 0.24 ± 0.35% |
| Cancer | 2.45% | 173.84% | 44.22 ± 35.28% | 0.00% | 0.89% | 0.05 ± 0.13% |
| Normal Colon | NA | NA | NA | 0.00% | 0.21% | 0.03 ± 0.04% |

MULTIPLEXED KRAS MUTATION DETECTION ASSAY

CROSS REFERENCE TO RELATED APPLICATIONS

This application is a continuation of U.S. patent application Ser. No. 14/811,266, filed on Jul. 28, 2015, which is a continuation of U.S. patent application Ser. No. 13/594,674, now issued as U.S. Pat. No. 9,127,318, which claims priority to the filing date of U.S. Provisional Patent Application Ser. No. 61/548,639 filed Oct. 18, 2011; which applications are herein incorporated by reference.

BACKGROUND

Germline KRAS mutations have been found to be associated with Noonan syndrome (Schubbert et al. Nat. Genet. 2006 38: 331-6) and cardio-facio-cutaneous syndrome (Niihori et al. Nat. Genet. 2006 38: 294-6). Likewise, somatic KRAS mutations are found at high rates in leukemias, colorectal cancer (Burmer et al. Proc. Natl. Acad. Sci. 1989 86: 2403-7), pancreatic cancer (Almoguera et al. Cell 1988 53: 549-54) and lung cancer (Tam et al. Clin. Cancer Res. 2006 12: 1647-53). Methods for the detection of point mutations in KRAS may be used, for example, to provide a diagnostic for cancer and other diseases.

SUMMARY

Provided herein is reagent mixture comprising multiplexed amplification reagents and flap assay reagents for detecting, in a single reaction, mutant copies of the KRAS gene that contain any of the 34A, 34C, 34T, 35A, 35C, 35T or 38A point mutations. Methods that employ the reagent mix and kits for performing the same are also provided.

BRIEF DESCRIPTION OF THE FIGURES

FIG. 3 schematically illustrates some of the general principles of an example of a subject assay.

FIG. 6 shows tables 3-6.

FIG. 7 shows the oligonucleotides used for multiplex detection and quantification of the seven mutant alleles of KRAS and the ACTB (beta actin) internal control. From top to bottom, SEQ ID NO: 30, SEQ ID NO: 17, SEQ ID NO: 22, SEQ ID NO: 4 (left), SEQ ID NO: 8 (right), SEQ ID NO: 23, SEQ ID NO: 15, SEQ ID NO: 5 (left), SEQ ID NO: 8 (right), SEQ ID NO: 16, SEQ ID NO: 24, SEQ ID NO: 6 (left), SEQ ID NO: 8 (right), SEQ ID NO: 13, SEQ ID NO: 25, SEQ ID NO: 1 (left), SEQ ID NO: 8 (right), SEQ ID NO: 11, SEQ ID NO: 26, SEQ ID NO: 2 (left), SEQ ID NO: 8 (right), SEQ ID NO: 12, SEQ ID NO: 27, SEQ ID NO: 3 (left), SEQ ID NO: 8 (right), SEQ ID NO: 14, SEQ ID NO: 28, SEQ ID NO: 7 (left), SEQ ID NO: 8 (right), SEQ ID NO: 18, SEQ ID NO: 29, SEQ ID NO: 9 (left), SEQ ID NO: 10 (right), SEQ ID NO: 19, SEQ ID NO: 20, and SEQ ID NO: 21.

DEFINITIONS

Figure 1:
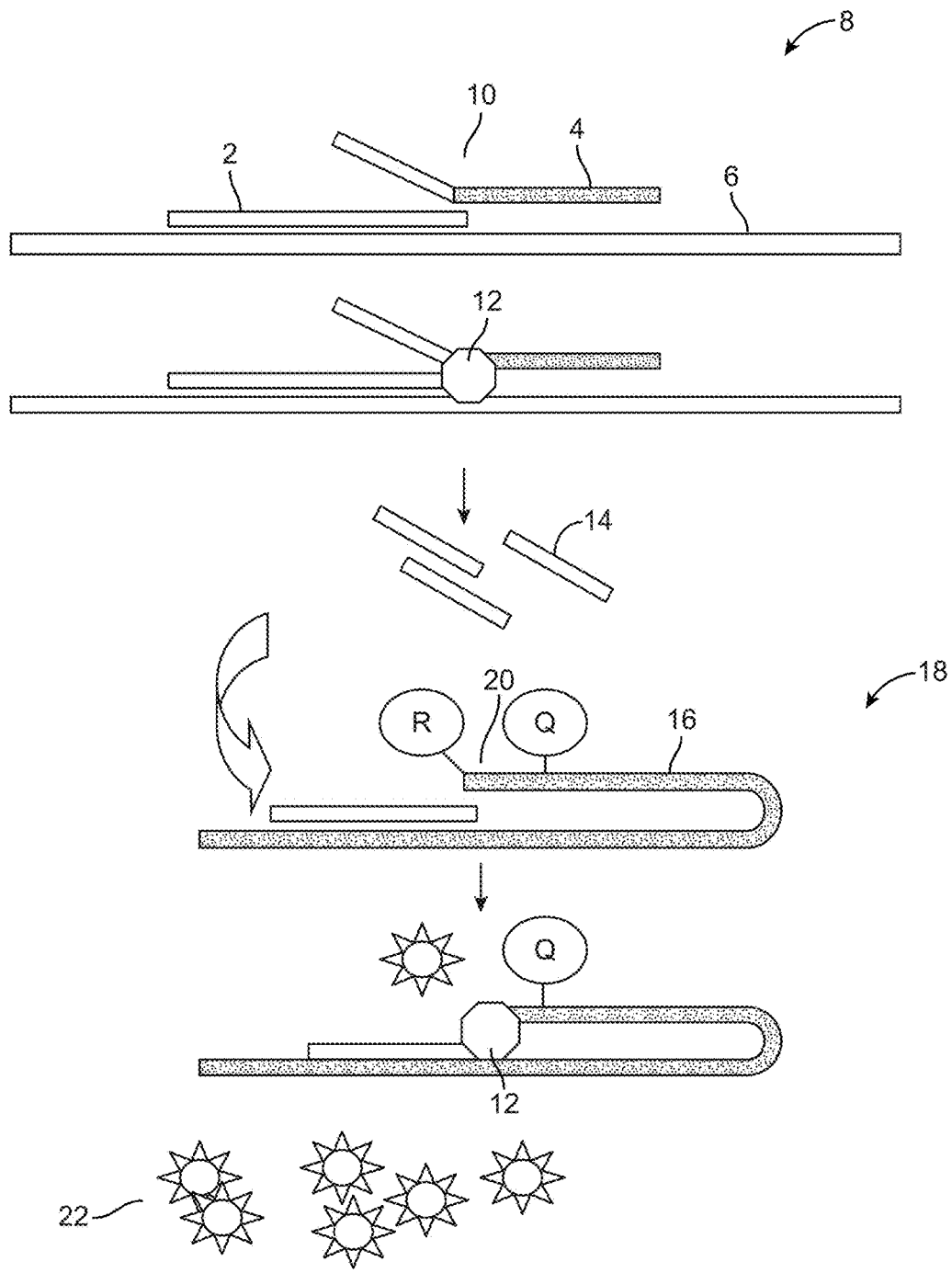
FIG. 1 schematically illustrates some of the general principles of a flap assay.

The term "sample" as used herein relates to a material or mixture of materials, typically, although not necessarily, in liquid form, containing one or more analytes of interest.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "nucleic acid sample," as used herein denotes a sample containing nucleic acid.

The term "target polynucleotide," as used herein, refers to a polynucleotide of interest under study. In certain embodiments, a target polynucleotide contains one or more target sites that are of interest under study.

The term "oligonucleotide" as used herein denotes a single stranded multimer of nucleotides of from about 2 to 200 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51 to 60, 61 to 70, 71 to 80, 80 to 100, 100 to 150 or 150 to 200 nucleotides in length, for example.

The term "duplex," or "duplexed," as used herein, describes two complementary polynucleotides that are base-paired, i.e., hybridized together.

The term "primer" as used herein refers to an oligonucleotide that has a nucleotide sequence that is complementary to a region of a target polynucleotide. A primer binds to the complementary region and is extended, using the target nucleic acid as the template, under primer extension conditions. A primer may be in the range of about 15 to about 50 nucleotides although primers outside of this length may be used. A primer can be extended from its 3' end by the action of a polymerase. An oligonucleotide that cannot be extended from it 3' end by the action of a polymerase is not a primer.

The term "extending" as used herein refers to any addition of one or more nucleotides to the end of a nucleic acid, e.g. by ligation of an oligonucleotide or by using a polymerase.

The term "amplifying" as used herein refers to generating one or more copies of a target nucleic acid, using the target nucleic acid as a template.

The term "denaturing," as used herein, refers to the separation of a nucleic acid duplex into two single strands.

The terms "determining", "measuring", "evaluating", "assessing," "assaying," "detecting," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and [$Na^+$] is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

As used herein, the term "$T_m$-matched" refers to a plurality of nucleic acid duplexes having $T_m$s that are within a defined range, e.g., within 5° C. or 10° C. of each other.

As used herein, the terms "reaction mixture" and "reagent mixture" refers to an aqueous mixture of reagents that are capable of reacting together to produce a product in appropriate external conditions over a period of time. A reaction mixture may contain PCR reagents and flap cleavage reagents, for example.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

As used herein, the term "flap assay" refers to an assay in which a flap oligonucleotide is cleaved in an overlap-dependent manner by a flap endonuclease to release a flap that is then detected. The principles of flap assays are well known and described in, e.g., Lyamichev et al. (Nat. Biotechnol. 1999 17:292-296), Ryan et al (Mol. Diagn. 1999 4:135-44) and Allawi et al (J Clin Microbiol. 2006 44: 3443-3447). For the sake of clarity, certain reagents that are employed in a flap assay are described below. The principles of a flap assay are illustrated in FIG. 1. In the flap assay shown in FIG. 1, an invasive oligonucleotide 2 and flap oligonucleotide 4 are hybridized to target 6 to produce a first complex 8 that contains a nucleotide overlap at position 10. First complex 8 is a substrate for flap endonuclease. Flap endonuclease 12 cleaves flap oligonucleotide 4 to release a flap 14 that hybridizes with FRET cassette 16 that contains a quencher "Q" and a nearby quenched flourophore "R" that is quenched by the quencher Q. Hybridization of flap 14 to FRET cassette 16 results in a second complex 18 that contains a nucleotide overlap at position 20. The second complex is also a substrate for flap endonuclease. Cleavage of FRET cassette 16 by flap endonuclease 12 results in release of the fluorophore 22, which produces a fluorescent signal. These components are described in greater detail below.

As used herein, the term "invasive oligonucleotide" refers to an oligonucleotide that is complementary to a region in a target nucleic acid. The 3' terminal nucleotide of the invasive oligonucleotide may or may not base pair a nucleotide in the target (e.g., which may be the site of a SNP or a mutation, for example).

As used herein, the term "flap oligonucleotide" refers to an oligonucleotide that contains a flap region and a region that is complementary to a region in the target nucleic acid. The target complementary regions on the invasive oligonucleotide and the flap oligonucleotide overlap by a single nucleotide such that, when they are annealed to the target nucleic acid, the complementary sequences overlap. As is known, if: a) the 3' terminal nucleotide of the invasive nucleotide and b) the nucleotide that overlaps with that nucleotide in the flap oligonucleotide both base pair with a nucleotide in the target nucleic acid, then a particular structure is formed. This structure is a substrate for an enzyme, defined below as a flap endonuclease, that cleaves the flap from the target complementary region of the flap oligonucleotide. If the 3' terminal nucleotide of the invasive oligonucleotide does not base pair with a nucleotide in the target nucleic acid, or if the overlap nucleotide in the flap oligononucleotide does not base pair with a nucleotide in the target nucleic acid, the complex is not a substrate for the enzyme and there is little or no cleavage.

The term "flap endonuclease" or "FEN" for short, as used herein, refers to a class of nucleolytic enzymes that act as structure specific endonucleases on DNA structures with a duplex containing a single stranded 5' overhang, or flap, on one of the strands that is displaced by another strand of nucleic acid, i.e., such that there are overlapping nucleotides at the junction between the single and double-stranded DNA. FENs catalyze hydrolytic cleavage of the phosphodiester bond at the junction of single and double stranded DNA, releasing the overhang, or the flap. Flap endonucleases are reviewed by Ceska and Savers (Trends Biochem. Sci. 1998 23:331-336) and Liu et al (Annu. Rev. Biochem. 2004 73: 589-615). FENs may be individual enzymes, multi-subunit enzymes, or may exist as an activity of another enzyme or protein complex, e.g., a DNA polymerase. A flap endonuclease may be thermostable.

As used herein, the term "cleaved flap" refers to a single-stranded oligonucleotide that is a cleavage product of a flap assay.

As used herein, the term "FRET cassette" refers to a hairpin oligonucleotide that contains a fluorophore moiety and a nearby quencher moiety that quenches the fluorophore. Hybridization of a cleaved flap with a FRET cassette produces a secondary substrate for the flap endonuclease. Once this substrate is formed, the 5' fluorophore-containing base is cleaved from the cassette, thereby generating a fluorescence signal.

As used herein, the term "flap assay reagents" refers to all reagents that are required for performing a flap assay on a substrate. As is known in the art, flap assays include an invasive oligonucleotide, a flap oligonucleotide, a flap endonuclease and a FRET cassette, as described above. Flap assay reagents may optionally contain a target to which the invasive oligonucleotide and flap oligonucleotide bind.

As used herein, the term "genomic locus" refers to a defined region in a genome. A genomic locus exists at the same location in the genomes of different cells from the same individual, or in different individuals. A genomic locus in one cell or individual may have a nucleotide sequence that is identical or very similar (i.e., more than 99% identical) to the same genomic locus in a different cell or individual. The difference in nucleotide sequence between the same locus in different cells or individuals may be due to one or more nucleotide substitutions. A SNP (single nucleotide polymorphism) is one type of point mutation that occurs at the same genomic locus between different individuals in a population. Point mutations may be somatic in that they occur between different cells in the same individual. A genomic locus mutation may be defined by genomic coordinates, by name, or using a symbol.

As used herein, a "site of a mutation" refers to the position of a nucleotide substitution in a genomic locus. Unless otherwise indicated, the site of a mutation in a nucleic acid can have a mutant allele or wild type allele of a mutation. The site of a mutation may be defined by genomic coordinates, or coordinates relative to the start codon of a gene (e.g., in the case of the "KRAS G35T mutation").

As used herein, the term "point mutation" refers to the identity of the nucleotide present at a site of a mutation in the mutant copy of a genomic locus. The nucleotide may be on either strand of a double stranded DNA molecule.

As used herein, the term "wild type", with reference to a genomic locus, refers to the alleles of a locus that contain a wild type sequence. In the case of a locus containing a SNP, the wild type sequence may contain the predominant allele of the SNP.

As used herein, the term "mutant", with reference to a genomic locus, refers to the alleles of a locus that contain a mutant sequence. In the case of a locus containing a SNP, the mutant sequence may contain a minor allele of the SNP. The mutant allele of a genomic locus may contain a nucleotide substitution that is not silent in that it either alters the expression of a protein or changes the amino acid sequence of a protein, which causes a phenotypic change (e.g., a cancer-related phenotype) in the cells that are heterozygous or homozygous for the mutant sequence relative to cells containing the wild type sequence. Alternatively, the mutant allele of a genomic locus may contain a nucleotide substitution that is silent.

As used herein, the term "corresponds to" and grammatical equivalents thereof in the context of, for example, a nucleotide in an oligonucleotide that corresponds to a site of a mutation, is intended to identify the nucleotide that is correspondingly positioned relative to (i.e., positioned across from) a site of a mutation when two nucleic acids (e.g., an oligonucleotide and genomic DNA containing the mutation) are hybridized. Again, unless otherwise indicated (e.g., in the case of a nucleotide that "does not base pair" or "base pairs" with a point mutation) a nucleotide that corresponds to a site of a mutation may base pair with either the mutant or wild type allele of a sequence.

As used herein, the term "KRAS" refers to the human cellular homolog of a transforming gene isolated from the Kirsten rat sarcoma virus, as defined by NCBI's OMIM database entry 190070.

A sample that comprises "both wild type copies of the KRAS gene and mutant copies of the KRAS gene" and grammatical equivalents thereof, refers to a sample that contains multiple DNA molecules of the same genomic locus, where the sample contains both wild type copies of the genomic locus (which copies contain the wild type allele of the locus) and mutant copies of the same locus (which copies contain the mutant allele of the locus). In this context, the term "copies" is not intended to mean that the sequences were copied from one another. Rather, the term "copies" in intended to indicate that the sequences are of the same locus in different cells or individuals.

As used herein the term "nucleotide sequence" refers to a contiguous sequence of nucleotides in a nucleic acid. As would be readily apparent, number of nucleotides in a nucleotide sequence may vary greatly. In particular embodiments, a nucleotide sequence (e.g., of an oligonucleotide) may be of a length that is sufficient for hybridization to a complementary nucleotide sequence in another nucleic acid. In these embodiments, a nucleotide sequence may be in the range of at least 10 to 50 nucleotides, e.g., 12 to 20 nucleotides in length, although lengths outside of these ranges may be employed in many circumstances.

As used herein the term "fully complementary to" in the context of a first nucleic acid that is fully complementary to a second nucleic acid refers to a case when every nucleotide of a contiguous sequence of nucleotides in a first nucleic acid base pairs with a complementary nucleotide in a second nucleic acid. As will be described below, a nucleic acid may be fully complementary to another sequence "with the exception of a single base mismatch", meaning that the sequences are otherwise fully complementary with the exception of a single base mismatch (i.e., a single nucleotide that does not base pair with the corresponding nucleotide in the other nucleic acid).

As used herein the term a "primer pair" is used to refer to two primers that can be employed in a polymerase chain reaction to amplify a genomic locus. A primer pair may in certain circumstances be referred to as containing "a first primer" and "a second primer" or "a forward primer" and "a reverse primer". Use of any of these terms is arbitrary and is not intended to indicate whether a primer hybridizes to a top strand or bottom strand of a double stranded nucleic acid.

The nucleotides of an oligonucleotide may be designated by their position relative to the 3' terminal nucleotide of an oligonucleotide. For example, the nucleotide immediately 5' to the 3' terminal nucleotide of an oligonucleotide is at the "−1" position, the nucleotide immediately 5' to the nucleotide at the −1 position is the "−2" nucleotide, and so on. Nucleotides that are "within 6 bases" of a 3' terminal nucleotide are at the −1, −2, −3, −4, −5 and −6 positions relative to the 3' terminal nucleotide.

DESCRIPTION OF EXEMPLARY EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In the following description, the skilled artisan will understand that any of a number of polymerases and flap endonucleases could be used in the methods, including without limitation, those isolated from thermostable or hyperthermostable prokaryotic, eukaryotic, or archaeal organisms. The skilled artisan will also understand that the enzymes that are used in the method, e.g., polymerase and flap endonuclease, include not only naturally occurring enzymes, but also recombinant enzymes that include enzymatically active fragments, cleavage products, mutants, and variants of wild type enzymes.

In further describing the method, the reagent mixture used in the method will be described first, followed by a description of the reaction conditions that may be used in the method.

Reagent Mixtures

A reagent mixture is provided. In certain embodiments, the reagent mixture comprises: a) amplification reagents comprising a thermostable polymerase, nucleotides, a set of at least seven forward primers, and a reverse primer, wherein: i. the 3' terminal nucleotide of each forward primer of the set base pairs with a different point mutation in the KRAS gene relative to other forward primers in the set, wherein the point mutation is selected from the following point mutations: 34A, 34C, 34T, 35A, 35C, 35T and 38A; ii. each of the forward primers comprises a nucleotide sequence that is fully complementary to a sequence in the KRAS gene with the exception of a single base mismatch within 6 bases of the 3' terminal nucleotide; and iii. each of the forward primers, in combination with the reverse primer, selectively amplifies a different allele of a KRAS gene, wherein the allele that is amplified is defined by the point mutation to which the 3' terminal nucleotide base pairs; and b) flap assay reagents comprising a flap endonuclease, a first FRET cassette that produces a fluorescent signal when cleaved, the set of at least seven forward primers, and a corresponding set of at least seven different flap oligonucleotides that each comprise a nucleotide that base pairs with one of the point mutations; wherein the reagent mixture is characterized in that, when the reagent mixture combined with a nucleic acid sample that comprises at least a 1,000-fold excess of wild type copies of the KRAS gene relative to mutant copies of the KRAS gene that contain one of the point mutations and thermocycled, the reagent mixture can amplify and detect the presence of the mutant copies of the KRAS gene in the sample. The reaction mixture is characterized in that it can amplify and detect the presence of mutant copies of the KRAS gene in the sample. The forward primers of the amplification reagents are employed as an invasive primer in the flap assay reagents.

The exact identities and concentrations of the reagents present in the reaction mixture may vary greatly but may be similar to or the same as those independently employed in PCR and flap cleavage assays, with the exception that the reaction mixture may contain $Mg^{2+}$ at a concentration that is higher than employed in conventional PCR reaction mixtures (which contain $Mg^{2+}$ at a concentration of between about 1.8 mM and 3 mM). In certain embodiments, the reaction mixture described herein contains $Mg^{2+}$ at a concentration of in the range of 4 mM to 10 mM, e.g., 6 mM to 9 mM. Exemplary reaction buffers and DNA polymerases that may be employed in the subject reaction mixture include those described in various publications (e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). Reaction buffers and DNA polymerases suitable for PCR may be purchased from a variety of suppliers, e.g., Invitrogen (Carlsbad, Calif.), Qiagen (Valencia, Calif.) and Stratagene (La Jolla, Calif.). Exemplary polymerases include Taq, Pfu, Pwo, UlTma and Vent, although many other polymerases may be employed in certain embodiments. Guidance for the reaction components suitable for use with a polymerase as well as suitable conditions for their use is found in the literature supplied with the polymerase. Primer design is described in a variety of publications, e.g., Diffenbach and Dveksler (PCR Primer, A Laboratory Manual, Cold Spring Harbor Press 1995); R. Rapley, (The Nucleic Acid Protocols Handbook (2000), Humana Press, Totowa, N.J.); Schena and Kwok et al., Nucl. Acid Res. 1990 18:999-1005). Primer and probe design software programs are also commercially available, including without limitation, Primer Detective (ClonTech, Palo Alto, Calif.), Lasergene (DNASTAR, Inc., Madison, Wis.), and Oligo software (National Biosciences, Inc., Plymouth, Minn.) and iOligo (Caesar Software, Portsmouth, N.H).

Exemplary flap cleavage assay reagents are found in Lyamichev et al. (Nat. Biotechnol. 1999 17:292-296), Ryan et al (Mol. Diagn. 1999 4:135-44) and Allawi et al (J Clin Microbiol. 2006 44: 3443-3447). Appropriate conditions for flap endonuclease reactions are either known or can be readily determined using methods known in the art (see, e.g., Kaiser et al., J. Biol. Chem. 274:21387-94, 1999). Exemplary flap endonucleases that may be used in the method include, without limitation, *Thermus aquaticus* DNA polymerase I, *Thermus thermophilus* DNA polymerase I, mammalian FEN-1, *Archaeoglobus fulgidus* FEN-1, *Methanococcus jannaschii* FEN-1, *Pyrococcus furiosus* FEN-1,

*Methanobacterium thermoautotrophicum Thermus thermophilus* FEN-1, CLEAVASE™ (Third Wave, Inc., Madison, Wis.), *S. cerevisiae* RTH1, *S. cerevisiae* RAD27, *Schizosaccharomyces pombe* rad2, bacteriophage T5 5'-3' exonuclease, *Pyroccus horikoshii* FEN-1, human exonuclease 1, calf thymus 5'-3' exonuclease, including homologs thereof in eubacteria, eukaryotes, and archaea, such as members of the class II family of structure-specific enzymes, as well as enzymatically active mutants or variants thereof. Descriptions of cleaving enzymes can be found in, among other places, Lyamichev et al., Science 260:778-83, 1993; Eis et al., Nat. Biotechnol. 19:673-76, 2001; Shen et al., Trends in Bio. Sci. 23:171-73, 1998; Kaiser et al. J. Biol. Chem. 274:21387-94, 1999; Ma et al., J. Biol. Chem. 275:24693-700, 2000; Allawi et al., J. Mol. Biol. 328:537-54, 2003; Sharma et al., J. Biol. Chem. 278:23487-96, 2003; and Feng et al., Nat. Struct. Mol. Biol. 11:450-56, 2004.

As noted above, the reaction mix contains reagents for assaying for, in a single vessel, seven different targets mutations in the KRAS gene. As such, the reaction mix contains multiple forward primers (the 3' bases of each of which base pairs with one of the seven point mutations), a single reverse primer, multiple different flap oligonucleotides that each have a nucleotide that base pairs with a single point mutation, and at least one FRET cassette for detecting flap cleavage. In one embodiment, flap oligonucleotides in a mixture may have a common flap to allow for, for example, the production of the same single fluorescent signal if any of the seven flap oligonucleotides is cleaved. In another embodiment, the flap assay reagents comprise a first FRET cassette and a second FRET cassette that produce distinguishable fluorescent signals when cleaved, and at least one of the at least seven different flap oligonucleotides comprises a flap sequence that hybridizes to the first FRET cassette and the remainder of said at least seven different flap oligonucleotides hybridizes to the second FRET cassette. In these embodiments, one fluorescent signal will indicate that one of the subset of the mutations is present, whereas the other fluorescent signal will indicate that one of the other mutations is present.

In certain cases the reagent mixture may contain a PCR primer pair, a flap oligonucleotide and FRET cassette for the detection of an internal control. In these embodiments, the reaction mixture may further comprise second amplification reagents and second flap reagents for amplifying and detecting a control sequence that is in a gene that is not in KRAS, wherein said second flap reagents comprise a second FRET cassette that produces a signal that is distinguishable from the signal of the first FRET cassette. In particular cases, the control gene may be β-actin, although any suitable sequence may be used.

Upon cleavage of the FRET cassettes, multiple distinguishable fluorescent signals may be observed. The fluorophore may be selected from, e.g., 6-carboxyfluorescein (FAM), which has excitation and emission wavelengths of 485 nm and 520 nm respectively, Redmond Red, which has excitation and emission wavelengths of 578 nm and 650 nm respectively and Yakima Yellow, which has excitation and emission wavelengths of 532 nm and 569 nm respectively, and Quasor670 which has excitation and emission wavelengths of 644 nm and 670 nm respectively, although many others could be employed.

As noted above, seven of the PCR primers (arbitrarily designated as the "forward" primers), comprises a 3' terminal nucleotide that base pairs with a point mutation (i.e., a mutant allele) in the genomic locus and also comprises a nucleotide sequence that is fully complementary to a sequence in the locus with the exception of a single base mismatch within 6 bases of the 3' terminal nucleotide (e.g., at the −1 position, the −2 position, the −3 position, the −4 position, the −5 position or the −6 position, relative to the 3' terminal nucleotide). In other words, in addition to having a 3' terminal nucleotide that base pairs with only the mutant allele of the mutation in the genomic locus, the primer also has a destabilizing mismatch near the 3' end that neither bases pairs with the mutant allele or the wild type allele of the genomic region. The mismatch may be at the same or different positions in each of the forward primers. Without being limited to any particular theory, the destabilizing mismatch is believed to destabilize hybridization of the 3' end of the first primer to the wild-type sequence to a greater extend than mutant sequence, thereby resulting in preferential amplification of the mutant sequence. As will be described in greater detail below, the presence of the product amplified using the first and second primers may be detected using a flap assay that employs the first primer or another oligonucleotide that has the destabilizing mutation and a terminal nucleotide that base pairs with only the mutant allele at the genomic locus. The use of such a sequence (i.e., a sequence that contains the destabilizing mutation and a terminal nucleotide that base pairs with only the mutant allele at the genomic locus) in the detection step provides further discrimination between mutant and wild type sequences in the amplification products. Without being bound to any particular theory, it is believed that the discrimination between mutant and wild type largely occurs in the first few rounds of amplification since the amplified sequence (i.e., the amplicon) provides a perfectly complementary sequence for the PCR primers to hybridize to. The wild type sequence should not be amplified, whereas the mutant sequence should be efficiently amplified. The length of the nucleotide sequence that is complementary to the KRAS gene in the forward primers may be at least 16 nucleotides in length (e.g., at least 17 nucleotides, at least 18 nucleotides, at least 19 nucleotides, to at least 10 nucleotides or more, in length).

The destabilizing mismatch can be done by substituting a nucleotide that base pairs with the point mutation with another nucleotide. The nucleotide that is substituted into the sequence may be another natural nucleotide (e.g., dG, dA, dT or dC), or, in certain circumstances, a modified nucleotide. In certain embodiments, the 3' end of the first primer may contain more than 1, e.g., 2 or 3, mismatches. In particular embodiments, the type of mismatch (e.g., whether the mismatch is a G:T mismatch or a C:T mismatch, etc.) used affects a primer's ability to discriminate between wild type and mutant sequences. In general terms, the order of the stabilities (from most stable to least stable) of various mismatches are as follows: G:T>G:G=A:G>T:G>G:A=T:T>T:C>A:C>C:T>A:A>C:A>C:C (as described in Gaffney and Jones (Biochemistry 1989 26: 5881-5889)), although the basepairs that surround the mismatch can affect this order in certain circumstances (see, e.g., Ke et al Nucleic Acids Res. 1993 21:5137-5143). The mismatch used may be optimized experimentally to provide the desired discrimination.

As would be apparent, the various oligonucleotides used in the method are designed so as to not interfere with each other. For example, in particular embodiments, the flap oligonucleotide may be capped at its 3' end, thereby preventing its extension. Further, in certain cases, the $T_m$s of the flap portion of the flap oligonucleotide and the target complementary regions of the flap oligonucleotide may independently be at least 10° C. lower (e.g., 10-20° C. lower) than the $T_m$s of the PCR primers, which results in a) less hybridization of the flap oligonucleotide to the target nucleic acid at higher temperatures (65° C. to 75° C.) and b) less hybridization of any cleaved flap to the FRET cassette at higher temperatures (65° C. to 75° C.), thereby allowing the genomic locus to be amplified by PCR at a temperature at which the flap does not efficiently hybridize.

In particular cases, the forward primers used for detection of the KRAS mutations may have at least 12 contiguous nucleotides (e.g. at least 13, 14, 15, 16, 17 or 18 contiguous nucleotides) starting from the 3' end of the following sequences: ACTTGTGGTAGTTGGAGCTCA (SEQ ID NO: 1), ACTTGTGGTAGTTGGAGCTCT (SEQ ID NO: 2), AACTTGTGGTAGTTGGAGATGC (SEQ ID NO: 3), CTTGTGGTAGTTGGAGCCA (SEQ ID NO: 4), CTTGTGGTAGTTGGAGCCT (SEQ ID NO: 5), TATAAACTTGTGGTAGTTGGACCTC (SEQ ID NO: 6), TGGTAGTTGGAGCTGGTAA (SEQ ID NO: 7). The flap probe may in certain cases base pair with 10 to 14 contiguous nucleotides, e.g., 11 to 13 contiguous nucleotides, of the KRAS gene.

In a multiplex reaction, the primers may be designed to have similar thermodynamic properties, e.g., similar $T_m$s, G/C content, hairpin stability, and in certain embodiments may all be of a similar length, e.g., from 18 to 30 nt, e.g., 20 to 25 nt in length. The other reagents used in the reaction mixture may also be $T_m$ matched.

The assay mixture may be present in a vessel, including without limitation, a tube; a multi-well plate, such as a 96-well, a 384-well, a 1536-well plate; and a microfluidic device. In certain embodiments, multiple multiplex reactions are performed in the same reaction vessel. Depending on how the reaction is performed, the reaction mixture may be of a volume of 5 µl to 200 µl, e.g., 10 µl to 100 µl, although volumes outside of this range are envisioned.

In certain embodiments, a subject reaction mix may further contain a nucleic acid sample. In particular embodiments, the sample may contain genomic DNA or an amplified version thereof (e.g., genomic DNA amplified using the methods of Lage et al, Genome Res. 2003 13: 294-307 or published patent application US20040241658, for example). In exemplary embodiments, the genomic sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the genomic sample may be from a formalin fixed paraffin embedded (FFPE) sample.

In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human, and it may be processed prior to use in the subject assay. For example, the nucleic acid may be extracted from the sample prior to use, methods for which are known.

For example, DNA can be extracted from stool from any number of different methods, including those described in, e.g, Coll et al (J. of Clinical Microbiology 1989 27: 2245-2248), Sidransky et al (Science 1992 256: 102-105), Villa (Gastroenterology 1996 110: 1346-1353) and Nollau (BioTechniques 1996 20: 784-788), and U.S. Pat. Nos. 5,463,782, 7,005,266, 6,303,304 and 5,741,650. Commercial DNA extraction kits for the extraction of DNA from stool include the QIAamp stool mini kit (QIAGEN, Hilden, Germany), Instagene Matrix (Bio-Rad, Hercules, Calif.), and Rapid-Prep Micro Genomic: DNA isolation kit (Pharmacia Biotech Inc., Piscataway, N.J.), among others.

Method for Sample Analysis

A method of sample analysis that employs the reagent mix is also provided. In certain embodiments, this method comprises: a) subjecting a reaction mixture comprising i. the above-summarized reagent mixture and ii. a nucleic acid sample that comprises at least a 100-fold excess of wild type copies of the KRAS gene relative to mutant KRAS gene that contain one of the point mutations, to the following thermocycling conditions: a first set of 5-15 cycles of: i. a first temperature of at least 90° C.; ii. a second temperature in the range of 60° C. to 75° C.; iii. a third temperature in the range of 65° C. to 75° C.; followed by: a second set of 20-50 cycles of: i. a fourth temperature of at least 90° C.; ii. a fifth temperature that is at least 10° C. lower than the second temperature; iii. a sixth temperature in the range of 65° C. to 75° C.; wherein no additional reagents are added to the reaction between the first and second sets of cycles and, in each cycle of the second set of cycles, cleavage of a flap probe is measured; and b) detecting the presence of a mutant copy of KRAS in the nucleic acid sample.

In these embodiments, the reaction mixture may be subject to cycling conditions in which an increase in the amount of amplified product (indicated by the amount of fluorescence) can be measured in real-time, where the term "real-time" is intended to refer to a measurement that is taken as the reaction progresses and products accumulate. The measurement may be expressed as an absolute number of copies or a relative amount when normalized to a control nucleic acid in the sample. Fluorescence can be monitored in each cycle to provide a real time measurement of the amount of product that is accumulating in the reaction mixture.

In some embodiments, the reaction mixture may be subjected to the following thermocycling conditions: a first set of 5 to 15 (e.g., 8 to 12) cycles of: i. a first temperature of at least 90° C.; ii. a second temperature in the range of 60° C. to 75° C. (e.g., 65° C. to 75° C.); iii. a third temperature in the range of 65° C. to 75° C.; followed by: a second set of 20-50 cycles of: i. a fourth temperature of at least 90° C.; ii. a fifth temperature that is at least 10° C. lower than the second temperature (e.g., in the range of 50° C. to 55° C.); and iii. a sixth temperature in the range of 65° C. to 75° C. No additional reagents need to be added to the reaction mixture during the thermocycling, e.g., between the first and second sets of cycles. In particular embodiments, the thermostable polymerase is not inactivated between the first and second sets of conditions, thereby allowing the target to be amplified during each cycle of the second set of cycles. In particular embodiments, the second and third temperatures are the same temperature such that "two step" thermocycling conditions are performed. Each of the cycles may be independently of a duration in the range of 10 seconds to 3 minutes, although durations outside of this range are readily employed. In each cycle of the second set of cycles (e.g., while the reaction is in the fifth temperature), a signal generated by cleavage of the flap probe may be measured to provide a real-time measurement of the amount of target nucleic acid in the sample.

Figure 2:
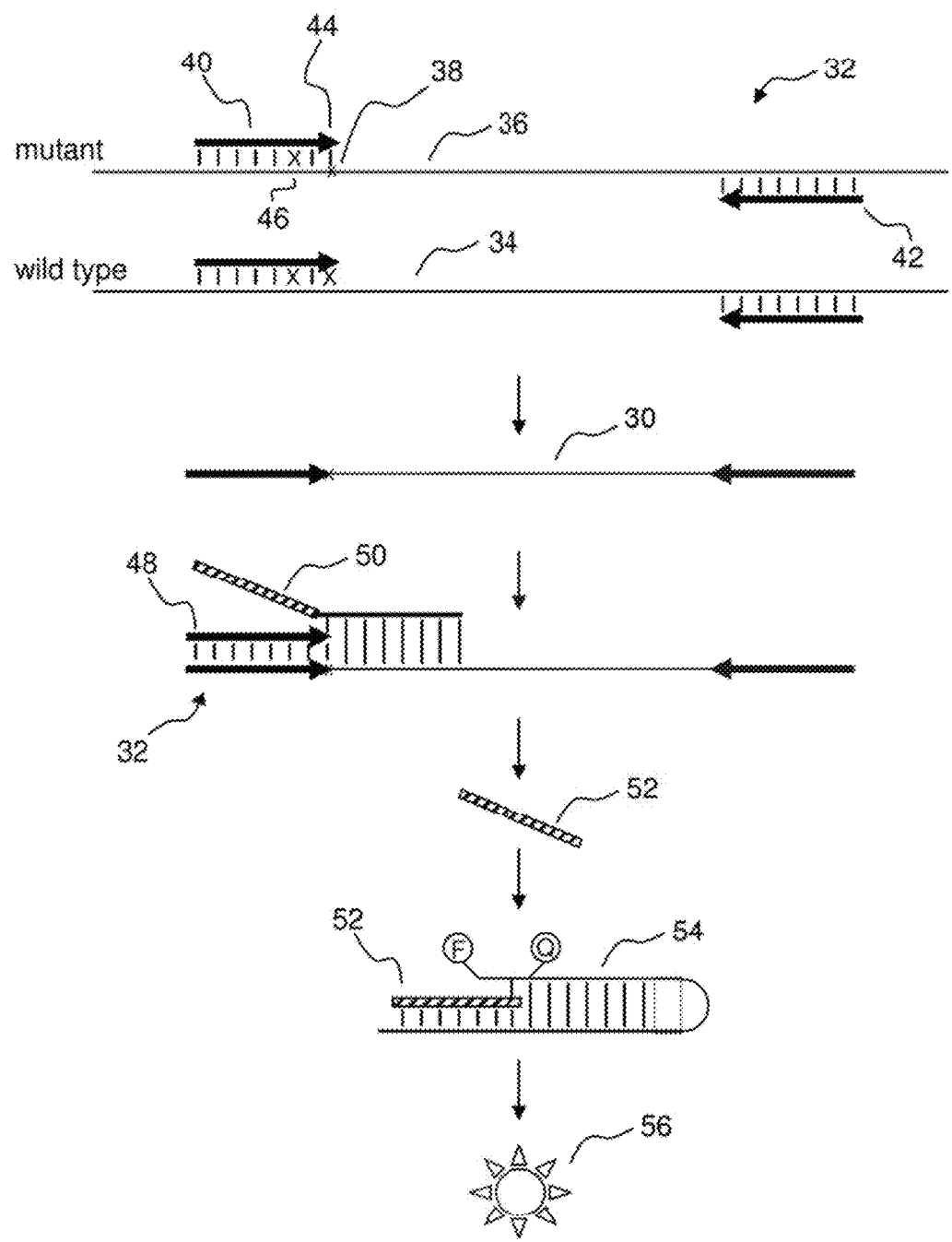
FIG. 2 schematically illustrates some of the general principles or one aspect of the subject method.

The method provided herein is a multiplexed invader assay that employs mismatched primers. The subject method may be readily adapted from the method shown in FIG. 2 by the addition of at least six other primers that recognize other point mutations in the KRAS gene, as described above. With reference to FIG. 2, the method includes amplifying product 30 from sample 32 that comprises both wild type copies of the KRAS gene 34 and mutant copies of the KRAS gene 36 that have a point mutation 38 (e.g., the 34A, 34C, 34T, 35A, 35C, 35T or 38A mutations) relative to the wild type gene 34, to produce an amplified sample. The amplifying is done using a forward primer 40 and a second primer 42, where the first primer comprises a 3' terminal nucleotide 44 that base pairs with the point mutation and also comprises a nucleotide sequence that is fully complementary to a sequence in the locus with the exception of a single base mismatch 46 (i.e., a base that is not complementary to the corresponding base in the target genomic locus) within 6 bases of 3' terminal nucleotide 44. The presence of product 30 in the amplified sample is detected using a flap assay that employs the same forward primer as an invasive oligonucleotide 48. As shown in FIG. 2, the forward primer 40 is employed as the invasive oligonucleotide 48 in the flap assay. As described above and in FIG. 1, the flap assay relies on the cleavage of complex 32 that contains a flap oligonucleotide 50, invasive oligonucleotide 48 and product 30 by a flap endonuclease (not shown) to release flap 52. Released flap 52 then hybridizes to FRET cassette 54 to form a second complex that is cleaved by the flap endonuclease to cleave the fluorophore from the complex and generate fluorescent signal 56 that can be measured to indicate the amount of product in the amplified sample. In this embodiment, the presence of a fluorescent signal indicates that there are mutant alleles of the KRAS gene in the sample.

The amount of product in the sample may be normalized relative to the amount of a control nucleic acid present in the sample, thereby determining a relative amount of the mutant copies of KRAS in the sample. In some embodiments, the control nucleic acid may be a different locus to the genomic locus and, in certain cases, may be detected using a flap assay that employs an invasive oligonucleotide having a 3' terminal nucleotide that base pairs with the wild type copies of the genomic locus at the site of the point mutation, thereby detecting the presence of wild type copies of the genomic locus in said sample. The control may be measured in parallel with measuring the product in the same reaction mixture or a different reaction mix. If the control is measured in the same reaction mixture, the flap assay may include further reagents, particularly a second invasive oligonucleotide, a second flap probe having a second flap and a second FRET cassette that produces a signal that is distinguishable from the FRET cassette used to detect the mutant sequence. In particular embodiments, the reaction mixture may further comprise PCR reagents and flap reagents for amplifying and detecting a second genomic locus or for detecting a second point mutation in the same genomic locus.

In certain cases, fluorescence indicating the amount of cleaved flap can be detected by an automated fluorometer designed to perform real-time PCR having the following features: a light source for exciting the fluorophore of the FRET cassette, a system for heating and cooling reaction mixtures and a fluorometer for measuring fluorescence by the FRET cassette. This combination of features, allows real-time measurement of the cleaved flap, thereby allowing the amount of target nucleic acid in the sample to be quantified. Automated fluorometers for performing real-time PCR reactions are known in the art and can be adapted for use in this specific assay, for example, the ICYCLER™ from Bio-Rad Laboratories (Hercules, Calif.), the Mx3000P™, the MX3005P™ and the MX4000™ from Stratagene (La Jolla, Calif.), the ABI PRISM™ 7300, 7500, 7700, and 7900 Taq Man (Applied Biosystems, Foster City, Calif.), the SMARTCYCLER™, ROTORGENE2000™ (Corbett Research, Sydney, Australia) the GENE XPERT™ System (Cepheid, Sunnyvale, Calif.) and the LIGHTCYCLER™ (Roche Diagnostics Corp., Indianapolis, Ind.). The speed of ramping between the different reaction temperatures is not critical and, in certain embodiments, the default ramping speeds that are preset on thermocyclers may be employed.

In certain cases, the method may further involve graphing the amount of cleavage that occurs in several cycles, thereby providing a real time estimate of the abundance of the nucleic acid target. The estimate may be calculated by determining the threshold cycle (i.e., the cycle at which this fluorescence increases above a predetermined threshold; the "Ct" value or "Cp" value). This estimate can be compared to a control (which control may be assayed in the same reaction mix as the genomic locus of interest) to provide a normalized estimate. The thermocycler may also contain a software application for determining the threshold cycle for each of the samples. An exemplary method for determining the threshold cycle is set forth in, e.g., Luu-The et al (Biotechniques 2005 38: 287-293).

A device for performing sample analysis is also provided. In certain embodiments, the device comprises: a) a thermocycler programmed to perform the above-described method and b) a vessel comprising the above-described reaction mixture.

Kits

Also provided are kits for practicing the subject method, as described above. The components of the kit may be present in separate containers, or multiple components may be present in a single container. In particular embodiments, a kit may comprise: a) amplification reagents comprising a thermostable polymerase, nucleotides, a set of at least seven forward primers, and a reverse primer, wherein: i. the 3' terminal nucleotide of each forward primer of the set base pairs with a different point mutation in the KRAS gene relative to other forward primers in the set, wherein the point mutation is selected from the following point mutations: 34A, 34C, 34T, 35A, 35C, 35T and 38A; ii. each of the forward primers comprises a nucleotide sequence that is fully complementary to a sequence in the KRAS gene with the exception of a single base mismatch within 6 bases of the 3' terminal nucleotide; and iii. each of the forward primers, in combination with the reverse primer, selectively amplifies a different allele of a KRAS gene, wherein the allele that is amplified is defined by the point mutation to which the 3' terminal nucleotide base pairs; and b) flap assay reagents comprising a flap endonuclease, a FRET cassette, the set of at least seven forward primers, and a corresponding set of at least seven different flap oligonucleotides that each comprise a nucleotide that base pairs with one of the point mutations. The particulars of these reagents are described above. The kit further comprises PCR and flap reagents for amplification and detection of a control nucleic acid.

In addition to above-mentioned components, the kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. In addition to instructions, the kits may also include one or more control samples, e.g., positive or negative controls analytes for use in testing the kit.

Utility

The method described finds use in a variety of applications, where such applications generally include sample analysis applications in which the presence of a mutant KRAS gene in a given sample is detected. In particular, the above-described methods may be employed to diagnose, to predict a response to treatment, or to investigate a cancerous condition or another mammalian disease, including but not limited to, a variety of cancers such as lung adenocarcinoma, mucinous adenoma, ductal carcinoma of the pancreas and colorectal carcinoma, Noonan syndrome, bladder cancer, gastric cancer, cardio-facio-cutaneous syndrome, leukemias, colon cancer, pancreatic cancer and lung cancer, for example.

In some embodiments, a biological sample may be obtained from a patient, and the sample may be analyzed using the method. In particular embodiments, the method may be employed to identify and/or estimate the amount of mutant copies of a genomic locus that are in a biological sample that contains both wild type copies of a genomic locus and mutant copies of the genomic locus that have a point mutation relative to the wild type copies of the genomic locus. In this example, the sample may contain at least 100 times (e.g., at least 1,000 times, at least 5,000 times, at least 10,000 times, at least 50,000 times or at least 100,000 times) more wild type copies of the KRAS gene than mutant copies of the KRAS gene.

Since the point mutation in the KRAS gene have a direct association with cancer, e.g., colorectal cancer, the subject method may be employed to diagnose patients with cancer or a pre-cancerous condition (e.g., adenoma etc.), alone, or in combination with other clinical techniques (e.g., a physical examination, such as, a colonoscopy) or molecular techniques (e.g., immunohistochemical analysis). For example, results obtained from the subject assay may be combined with other information, e.g., information regarding the methylation status of other loci, information regarding rearrangements or substitutions in the same locus or at a different locus, cytogenetic information, information regarding rearrangements, gene expression information or information about the length of telomeres, to provide an overall diagnosis of cancer or other diseases.

In additional embodiments, if a KRAS mutation is detected in a sample, the identity of the mutation in the sample may be determined. This may be done by, e.g., sequencing part of the KRAS locus in the sample, or by performing seven separate assays (i.e., using the same reagents, but not in multiplex form) to determine which of the mutations is present.

In one embodiment, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may include a Ct value, or Cp value, or the like that indicates the presence of mutant copies of the genomic locus in the sample. Once generated, the report may be forwarded to another location (which may the same location as the first location), where it may be interpreted by a health professional (e.g., a clinician, a laboratory technician, or a physician such as an oncologist, surgeon, pathologist), as part of a clinical diagnosis.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Example 1

Materials and Methods

Colorectal cancer (CRC) is the second leading cause of cancer deaths in the United States, yet with effective screening it is potentially the most treatable and preventable cancer (JNCI 2010; 102:89, Ann Intern Med 2009; 150:1, Ann Intern Med 2008; 149:441).

The aim of this study was to evaluate the performance of the mutation detection component of an assay by testing a set of colorectal tissues that were characterized using standard dideoxynucleotide sequencing. The assay is designed to detect the common KRAS mutation sequences at Codons 12 and 13, which are found in approximately 35% of all colorectal cancer tissues. The current assay combines all seven KRAS mutations in a single reaction. ACTB (beta-actin) is also included in the reaction to confirm sufficient DNA levels and to ratio KRAS against to establish percent mutation.

A multiplexed KRAS assay was designed utilizing QuARTS (Quantitative Allele-specific Real-time Target and Signal amplification), a highly sensitive technology that combines allele-specific DNA amplification with invasive cleavage chemistry to generate signal during each amplification cycle similar to real-time PCR. The assay, which detects seven KRAS mutations and the reference gene β-actin, was used to assess 87 colorectal tissue samples (52 CRCs, 16 adenomas≥1 cm, and 19 normal epithelia) as determined by Mayo Clinic Pathology. Samples were obtained by microdissection of fresh frozen tissue biopsies. DNA was extracted by Mayo Clinic using a standardized chloroform/phenol methodology. The genotypes of each sample were established using dye terminator dideoxynucleotide sequencing in both the forward and reverse orientations. Copy numbers of KRAS mutations and β-actin were determined by conventional comparison against standard curves. KRAS data are reported as percent mutation and calculated by dividing mutant copies by β-actin copies and multiplying by 100.

Tissue Sample Excising, Extraction, and Sequencing

Tissue samples were collected from adenoma and primary tumors and normal colons at the Mayo Clinic with IRB approval. Patients with confirmed neoplasia had been identified by colonoscopy, endoscopy, radiologic, and/or ultrasound studies. Normal colonic tissue samples were collected from colonoscopy negative patients. For the tumors, pathologist examined the tissue sections and circled out histologically distinct lesions to direct careful micro-dissection with about 80% purity. DNA was extracted at Mayo Clinic using either the QIAamp DNA Micro Kit (PN 56304 Germantown, Md.) or a standardized chloroform/phenol methodology. Tissue DNAs were stored at −80° C.

Sequencing

The KRAS genotypes of each cancer or adenoma sample were established using dye terminator dideoxynucleotide sequencing in both the forward and reverse orientations for a region including codons 12 and 13 of the KRAS gene.

Samples were sequenced on an ABI 3730XL DNA Analyzer using Big Dye Terminator v3.1 reagents (Applied Biosystems). Mutation Surveyor v3.30 software (SoftGenetics) was used to make the calls. Lane quality scores for the traces were greater than 20, indicating less than 5% average background noise, and base calls were made based on signal to noise ratios, peak heights, overlap, and drop-off rate. When quality scores were above 20 in both directions, concurrence in both directions was required to verify an alteration from wild type (WT). If one direction was of low quality, but the other was above the threshold of 20, the single high quality read was sufficient to make a call. Traces were manually inspected for accuracy and 2 positive calls were made which were below the sensitivity of the software. Normal colon samples were not sequenced. Only mutation 34C was not represented in these samples.

QuARTS Assay Techniques

DNA samples extracted from tissues were assessed for the presence of mutations in exon 2 of the KRAS gene (See Table 1) and the reference gene Beta-Actin using a multiplexed QuARTS (Quantitative Allele-specific Real-time Target and Signal amplification) assay.

TABLE 1

| KRAS Mutation | KRAS mutation short form | Codon Location | Amino acid in mutation | Amino acid change | Amino acid in KRAS WT |
|---|---|---|---|---|---|
| 35G > A | 35A | Codon 12 | Aspartate | Gly12Asp | Glycine |
| 35G > T | 35T | Codon 12 | Valine | Gly12Val | |
| 34G > T | 34T | Codon 12 | Cystine | Gly12Cys | |
| 35G > C | 35C | Codon 12 | Alanine | Gly12Ala | |
| 34G > A | 34A | Codon 12 | Serine | Gly12Ser | |
| 34G > C | 34C | Codon 12 | Arginine | Gly12Arg | |
| 38G > A | 38A | Codon 13 | Aspartate | Gly13Asp | |

The assay is specific to the mutant KRAS DNA and is able to discriminate mutants from wild-type with low cross-reactivity. Specificity is achieved by the use of allele specific PCR with specific mismatches in the forward primer to preferentially amplify mutant alleles combined with semi-quantitative invasive cleavage reactions that further discriminate and detect the amplified target using real-time fluorescence detection.

The QuARTS reaction was optimized so the primers and probes for each mutation would function properly at same cycling and reaction conditions allowing all eight markers to be combined in a single reaction. Cycling conditions are designed to preferentially amplify mutant sequences by using a higher annealing temperature in the first 10 cycles, followed by 35 cycles at lower annealing temperature required for the invasive cleavage reaction. Fluorescent acquisition begins after the first 10 cycles. Multiplex KRAS assays were first optimized in a two-dye configuration where all mutations reported to one dye while ACTB reported to a second dye. The assay was further optimized to improve specificity and sensitivity by moving to a 3-dye configuration. The 3-dye KRAS QuARTS multiplex is configured to report to different dyes so that 4 mutations report to one dye (G35A, G35C, G34A, and G34C), 3 report to a second dye (G35T, G34T and G38A), and ACTB reports to a third dye (see FIG. 3).

The KRAS QuARTS multiplex technology generates highly sensitive and specific signal from mutant KRAS sequences and a beta-actin reference gene by utilizing two simultaneous reactions (FIG. 3). In the first reaction, allele-specific amplification is achieved with a unique forward primer for each mutation in combination with a single KRAS reverse primer. Each forward primer contains a double mismatch to the KRAS WT sequence near the 3' end of the primer, which prevents efficient amplification of KRAS WT, but has only a single mismatch to the mutation sequence. Taq (recombinant Hot Start Go Taq, Promega, Madison, Wis.) is able to extend efficiently through a single mismatch but not through a double mismatch near the 3' end. Signal generation occurs in the second reaction. A target specific probe binds to the mutant amplicon to form an overlap flap substrate. The 5' flap is then cleaved by the Cleavase enzyme (Hologic, Madison, Wis.). The flap sequence is complementary to a FRET cassette. Once the flap is cleaved, it binds to the target FRET cassette and causes the release of the fluorophore to generate signal. The seven KRAS probes share two different flap sequences, which report to either a HEX or FAM FRET cassette. A probe specific to beta-actin contains a third flap sequence and reports to Quasar 670 FRET cassette. The use of 3 different flap sequences that correspond to a FAM, HEX or Quasar 670 FRET cassette allows the assay to distinguish KRAS mutations from the beta-actin reference gene in a single well. In total, the KRAS multiplex QuARTS assay combines seven KRAS forward primers, a single KRAS reverse primer, 7 KRAS probes, a beta-actin forward and reverse primer, and three FRET cassettes. The concentration ranges for primers are from 105 to 245 nM, probes are from 90 to 250 nM, and FRET cassettes are at 100 nM each.

Figure 4:
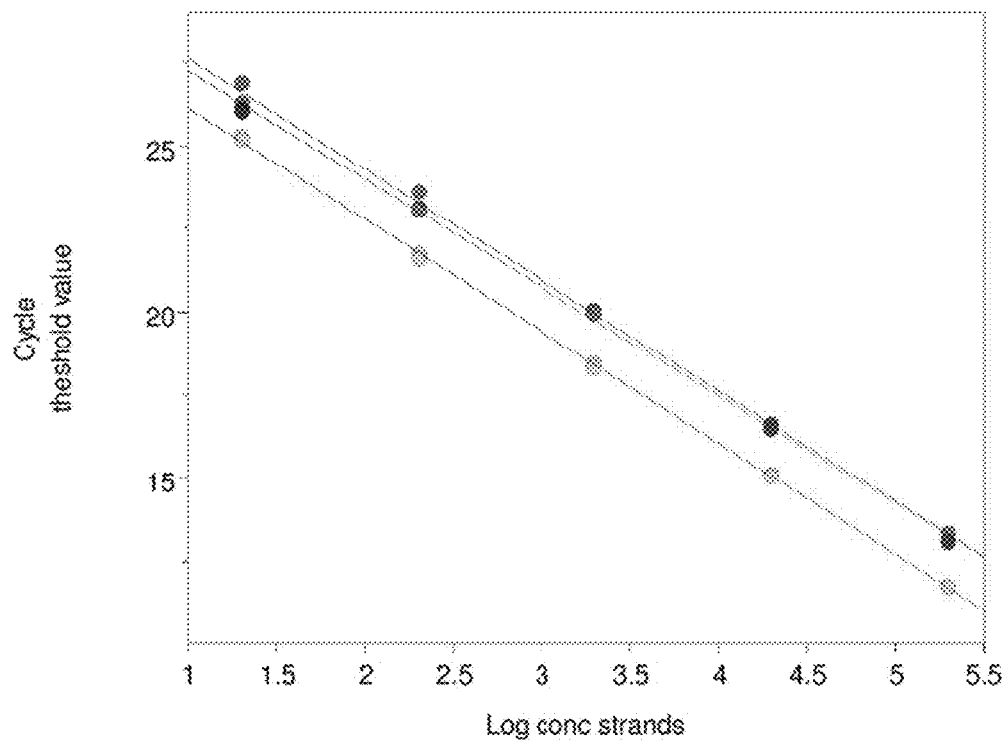
FIG. 4 shows standard curves for both KRAS mutation calibrators, 35C reporting to HEX (Yellow; bottom line)) and 38A reporting to FAM (Green; top line)), and the ACTB calibrator reporting to Quasar 670 (Red; middle line), show good linearity across 5-logs, from 100,000 copies per reaction to 10 copies per reaction. All three markers show similar slopes and intercept values.

Reactions were setup by adding 10 µL of DNA from each sample to appropriate wells of a 96-well plate containing 20 µL of assay-specific QuARTS™ master mix. Each plate was run on an ABI 7500 Fast Dx Real-Time PCR Instrument. Calibrators and controls were included in each run. After the run was completed, data was exported to an Exact Sciences analysis template, and the cycle threshold value was calculated as the cycle at which the fluorescent signal per channel for a reaction crosses a threshold of 18% of the maximum fluorescence for that channel DNA strand number was determined by comparing the cycle threshold of the target gene to the calibrator curve for that assay. Calibrators were made from plasmids with single target inserts, mutation 38A was used for the FAM channel and 35C was used for the HEX channel Percent mutation was determined for each marker by dividing KRAS strands by ACTB strands and multiplying by 100. All mutations reporting to the FAM dye are quantified using KRAS 38A calibrators, and all mutations reporting to the HEX dye are quantified using KRAS 35C calibrators. The calibrators for all three dyes show similar linearity (FIG. 4) and good reproducibility. The assay was optimized to minimize cross-reactivity with KRAS WT plasmid at 200,000 strands per reaction, which was approximately 0.07 to 0.11 percent mutation in the 3-dye configuration.

Results

The 2-dye KRAS multiplex QuARTS assay was evaluated using 87 tissue samples consisting of 19 normal, 16 adenoma and 52 colorectal cancer samples. KRAS QuARTS results showed good agreement with sequencing data. All normal colon samples had a value equal to or less than 0.55 percent mutation. All of the samples that were KRAS positive by sequencing were greater than 8.35 percent mutation. The colorectal cancer and adenoma samples that were KRAS negative by sequencing showed a range from 0.04 to 1.33 percent mutation with a mean of 0.4±0.29%. (Tables 3 and 4; shown in FIG. 6).

The 3-dye KRAS multiplex QuARTS assay was evaluated using 191 tissue samples consisting of 47 normal, 48 adenoma, and 96 colorectal cancer samples (Tables 2 below and Tables 5 and 6 shown in FIG. 6). This set included 86 of the 87 tissues that were also tested with the 2-dye configuration (Table 4; shown in FIG. 6). KRAS QuARTS showed excellent agreement with sequencing data. All of the samples that were KRAS positive by sequencing showed at least 2.45 percent mutation in the KRAS QuARTS assay, with a mean of 43.73±33.3 percent mutation. The colorectal cancer and adenoma samples that were negative by sequencing showed a range from 0.00 to 1.99 percent mutation with a mean of 0.14±0.33 percent mutation. The adenoma sample that showed 1.99 percent mutation was detected at 1.33 percent mutation in the 2-dye configuration. All normal colon samples had a value equal to or less than 0.21 percent mutation (mean for normal samples was 0.03±0.04 percent mutation).

TABLE 2

Sequence and QuARTS assay data concordance: Subset of Tissue DNA

| Sample name | Colon tissue histology | Average ACTB strands per reaction | % mutation FAM Channel | % mutation HEX channel | Genotype |
|---|---|---|---|---|---|
| TS1 | Cancer | 11090 | 2.45% | 1.04% | 35A |
| TS2 | Adenoma | 5187 | 11.74% | 6.30% | 35A |
| TS3 | Cancer | 2180 | 19.29% | 0.03% | 35T |
| TS4 | Adenoma | 1172 | 37.80% | 0.02% | 35T |
| TS5 | Cancer | 46798 | 55.69% | 0.00% | 38A |
| TS6 | Cancer | 64399 | 3.46% | 61.78% | 34A |
| TS7 | Adenoma | 3349 | 16.16% | 19.20% | 35A |
| TS8 | Cancer | 7578 | 12.60% | 0.00% | 34T |
| TS9 | Adenoma | 18667 | 1.99% | 0.07% | WT |
| TS10 | Cancer | 52344 | 0.06% | 0.00% | WT |
| TS11 | Cancer | 20977 | 0.02% | 0.00% | WT |
| TS12 | Adenoma | 51648 | 0.01% | 0.52% | WT |
| TS13 | Adenoma | 43957 | 0.03% | 0.01% | WT |
| TS14 | Adenoma | 98260 | 0.12% | 0.30% | WT |
| TS15 | Normal colon | 21484 | 0.00% | 0.00% | WT |
| TS16 | Normal colon | 92492 | 0.03% | 0.00% | WT |
| TS17 | Normal colon | 13228 | 0.01% | 0.00% | WT |
| TS18 | Normal colon | 579 | 0.00% | 0.00% | WT |
| TS19 | Normal colon | 211699 | 0.00% | 0.18% | WT |
| TS20 | Normal colon | 85889 | 0.01% | 0.02% | WT |
| TS21 | Adenoma | 4097 | 63.83% | 41.74% | 34T; 35C |
| TS22 | Cancer | 1806 | 101.96% | 0.00% | 38A |
| TS23 | Adenoma | 1864 | 1.37% | 43.58% | 34A |
| TS24 | Adenoma | 6433 | 48.83% | 4.70% | 35T |

The KRAS QuARTS multiplex assay showed a maximum of 0.11 percent mutation for cross-reactivity with KRAS WT plasmid control at 200,000 strands per reaction.

Figure 5:
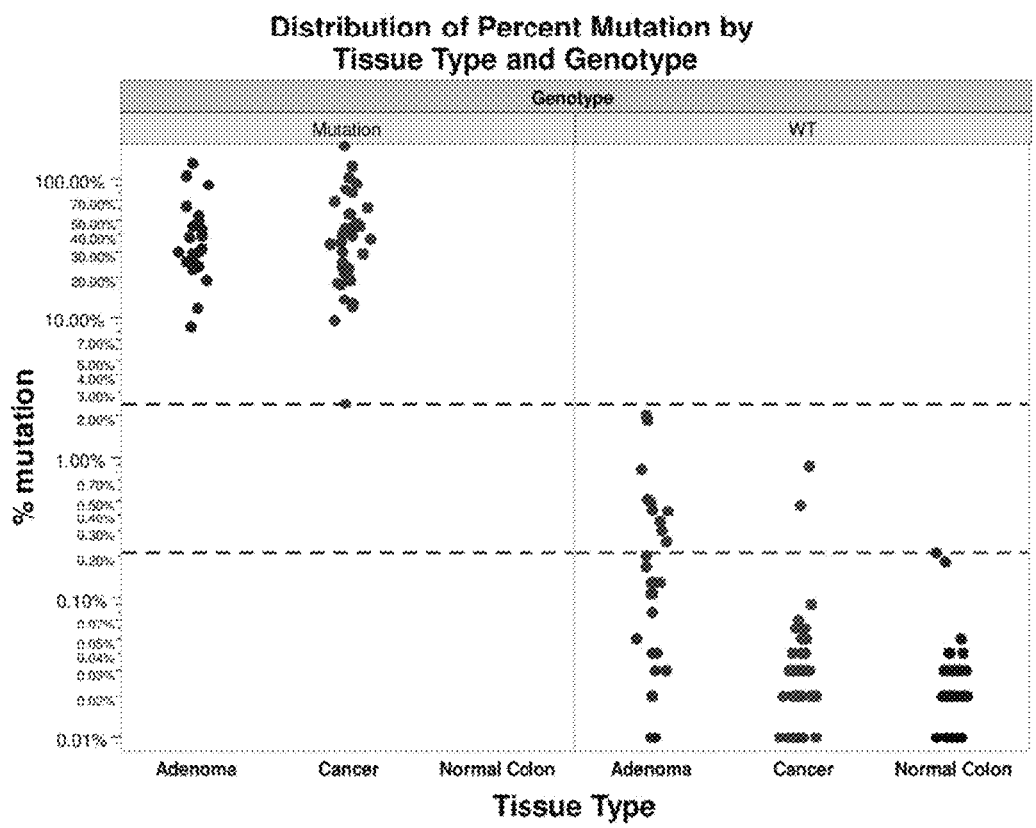
FIG. 5 is a graph showing the distribution of percent mutation by sample type.

FIG. 5 shows the distribution of percent mutation by sample type. With the highest normal giving 0.21 percent and the lowest sequencing confirmed KRAS mutation at 2.45 percent the assay agrees 100% on those samples. Because of the higher sensitivity of the QuARTS assay 2 cancers and 12 adenomas are observed that are elevated above the highest percent mutation of the normal samples.

Based on sequencing data: the 52 CRC samples contained 22 KRAS mutations and 30 wild-type genotypes, the 16 adenomas≥1 cm contained 8 mutations and 8 wild-type genotypes, and the 19 normal tissues contained all wild-type genotypes. The QuARTS assay detected 100% of the KRAS mutations in the CRC and adenomas and provided excellent differentiation between wild-type and mutation, with the highest percent KRAS mutation of normal wild-type samples at 0.55% and the lowest percent mutation of KRAS positive samples at 8.34%. Based on this data, this assay is more sensitive analytically than standard sequencing.

In this study we were able to show results for 6 of the 7 mutations detected by the assay; mutation 34C (Gly12Arg) in exon 2 represents 0.5% of KRAS mutations in colorectal cancers and was not represented in these samples. Using plasmid derived sequences we have shown the assay is capable of detecting this mutation (data not shown).

This multiplex does not distinguish among mutations. The assay shows some cross-reactivity between mutations which is likely to improve sensitivity since the signal is increased without any increase in WT cross reactivity.

The three-dye configuration of the KRAS QuARTS multiplex assay showed better specificity than the 2-dye version; when all KRAS mutations are reporting to a single dye, the signal from cross-reactivity with WT is additive but by distributing the KRAS mutation signal across two dyes, the cross-reactivity with WT is reduced by more than half.

Example 2

Materials and Methods

Figure 7:
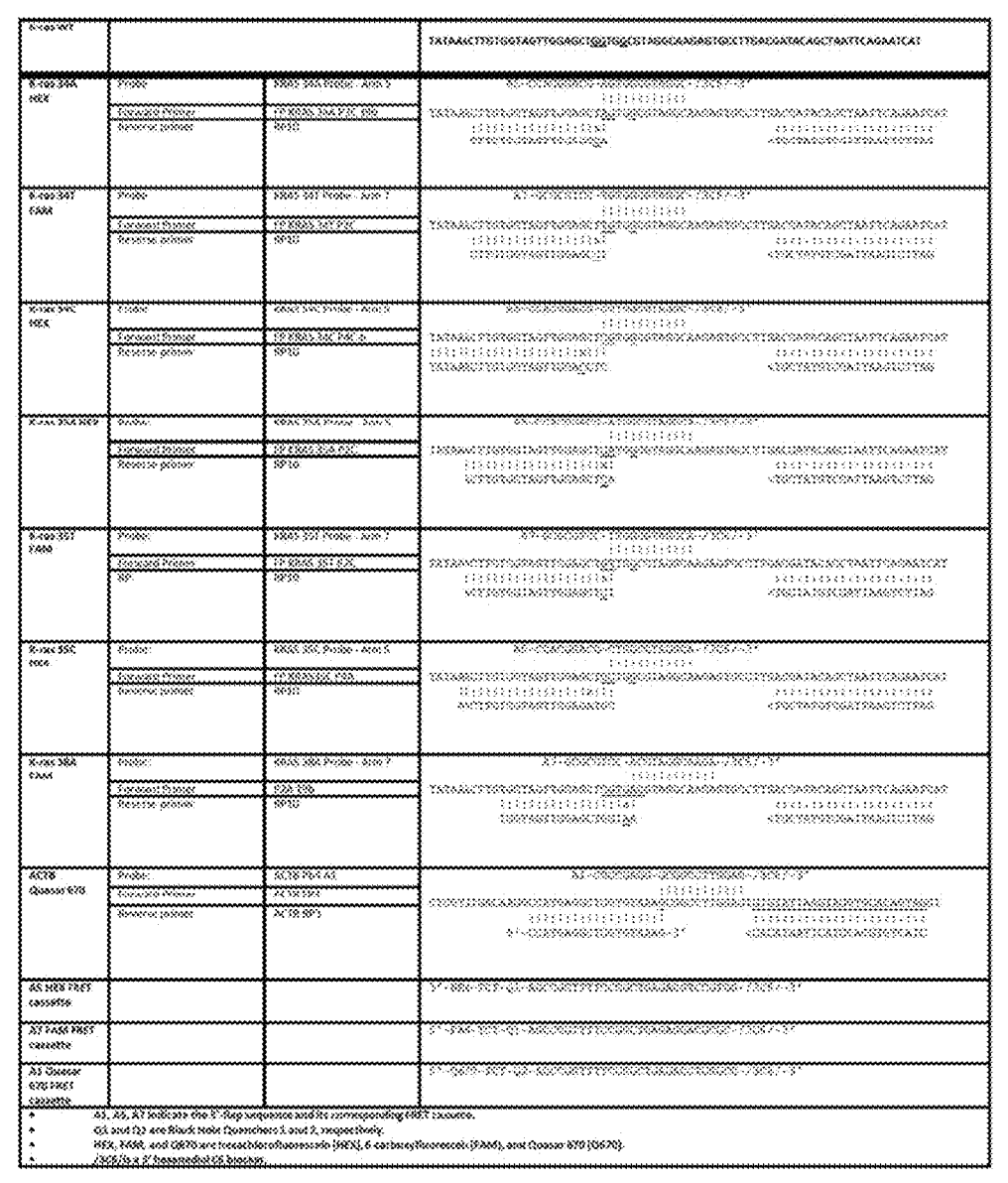

FIG. 7 shows the designs used for multiplex detection and quantification of the seven mutant alleles of KRAS and the ACTB (beta actin) internal control. Three 5'-flaps (A5 and A7 for KRAS and A1 for ACTB) were used in the assay. The probes with flaps A5 and A7, used for KRAS mutants, were used in conjunction with two FRET oligonucleotides A5-HEX and A7-FAM thus giving signal in these two dye channels for KRAS mutations. The ACTB probe, on the other hand, had a 5'-flap A1-Quasar, resulting in Quasar 670 signal when ACTB is present. Further details of the reagent mix are set forth below.

Reagent Mix Components
Mutation QuARTS Assay Primers

| Primer Name | Sequence | Conc in final reaction (nM) |
|---|---|---|
| KRAS RP10 | GATTCTGAATTAGCTGTATCGT (SEQ ID NO: 8) | 350 |
| KRAS 35A P2C | ACTTGTGGTAGTTGGAGCTCA (SEQ ID NO: 1) | 250 |
| KRAS 35T P2C | ACTTGTGGTAGTTGGAGCTCT (SEQ ID NO: 2) | 250 |
| KRAS 35C P4A | AACTTGTGGTAGTTGGAGATGC (SEQ ID NO: 3) | 250 |
| KRAS 34A P2C 19b | CTTGTGGTAGTTGGAGCCA (SEQ ID NO: 4) | 250 |
| KRAS 34T P2C | CTTGTGGTAGTTGGAGCCT (SEQ ID NO: 5) | 250 |
| KRAS 34C P4C-b | TATAAACTTGTGGTAGTTGGACCTC (SEQ ID NO: 6) | 250 |
| KRAS 38A P2A 19b | TGGTAGTTGGAGCTGGTAA (SEQ ID NO: 7) | 250 |
| ACTB WT FP3 | CCATGAGGCTGGTGTAAAG (SEQ ID NO: 9) | 150 |
| ACTB WT RP3 | CTACTGTGCACCTACTTAATACAC (SEQ ID NO: 10) | 150 |

Mutation QuARTS Assay Probes

| Probes | Probe sequence | Conc in final reaction (nM) |
|---|---|---|
| KRAS 35T A7 Pb | GCGCGTCCTTGGCGTAGGCA/3C6/ (SEQ ID NO: 11) | 310 |
| KRAS 35C A5 Pb | CCACGGACGCTGGCGTAGGCA/3C6/ (SEQ ID NO: 12) | 310 |
| KRAS 35A A5 Pb | CCACGGACGATGGCGTAGGCA/3C6/ (SEQ ID NO: 13) | 310 |
| KRAS 38A A7 Pb | GCGCGTCCACGTAGGCAAGA/3C6/ (SEQ ID NO: 14) | 310 |
| KRAS 34T A7 Pb | GCGCGTCCTGTGGCGTAGGC/3C6/ (SEQ ID NO: 15) | 310 |
| KRAS 34C AS Pb | CCACGGACGCGTGGCGTAGGC/3C6/ (SEQ ID NO: 16) | 310 |
| KRAS 34A AS pb | CCACGGACGAGTGGCGTAGGC/3C6/ (SEQ ID NO: 17) | 310 |
| ACTB WT Pb4 A1 | CGCCGAGGGCGGCCTTGGAG/3C6/ (SEQ ID NO: 18) | 310 |

FRET Cassettes— all FRET sequences exactly match the arm landing pad (no extra 3' bases)

| name | sequence 5'-3' | Conc in final reaction (nM) |
|---|---|---|
| Arm 5 TAMRA FRET | TAMRA/TCT/BHQ2/AGCCGGTTTT CCGGCTGAGACGTCCGTGG/3C6/ (SEQ ID NO: 19) | 100 |
| Arm 7 FAM FRET | FAM/TCT/BHQ1/AGCCGGTTTTCC GGCTGAGAGGACGCGC/3C6/ (SEQ ID NO: 20) | 100 |
| Arm 1 Quasar 670 FRET | Quasar 670/TCT/BHQ2/AGCCG GTTTTCCGGCTGAGACCTCGGCG/ 3C6/ (SEQ ID NO: 21) | 100 |

Other Components

| Current reaction buffer components | |
|---|---|
| Reagents | Concentration per reaction |
| recombinant HotStart Go Taq | 0.07 U/uL |
| water, PM1009 | NA |
| PM1143, Elution Buffer | Teknova Te pH 8.0 buffer + 20 ng/uL tRNA |
| dNTPs* | 250 μM |
| MOPS | 10 mM |
| 1M KCl | 0.797 mM |
| 2M MgCl2 | 7.5 mM |
| 5M Tris-HCl pH 8 | 0.319 mM |
| 50% Tween-20 | 0.008% |
| 20% IGEPAL | 0.008% |
| 80% glycerol | 1.25% |
| Cleavase | 7.3 ng/uL |
| BSA | 100 ng/uL (3 ug/30 uL reaction) |

*likely to be part of oligo mix rather than 20X reaction buffer

Thermocycling Parameters

| Stage | Temp/Time | Ramp Rate | Number of Cycles |
|---|---|---|---|
| Pre-incubation | 95° C./3' | 100% | 1 |
| Amplification 1 | 95° C./20" | 100% | 10 |
| | 64° C./30" | 100% | |
| | 70° C./30" | 100% | |
| Amplification 2 | 95° C./20" | 100% | 35 |
| | 53° C./1' | 100% | |
| | 70° C./30" | 100% | |
| Cooling | 40° C./30" | 100% | 1 |

Results

Using an oligonucleotide mixture with three FRET oligonucleotides (FAM or HEX with Quasar) and one KRAS mutant and ACTB specific oligonucleotide mixture, it was found that signal is generated for ACTB only when ACTB is present. However, for KRAS, it was found that cross-reactive signal is generated in HEX and FAM channels between some mutant KRAS mutations (see table below) with minimal cross-reactivity signal for wild-type KRAS. For example, when the target is KRAS 34C mutation, the 35A and 35T oligonucleotide mixtures gave appreciable cross-reactive signal. The table below shows the results reported as cycle threshold values obtained using 1,000 copies of the different KRAS mutants, and 10,000 copies for ACTB targets with either duplex or multiplex oligonucleotide mixes. Based on these results, and based on the low cross reactivity of 35C and 38A targets, those two targets were selected to be the calibrators used for standard curve generation.

| Reporting Dyes | Oligo mix: | | Target: 34A 1 | 34C 2 | 34T 3 | 35 4 | 35C 5 | 35T 6 | 38A 7 | ACTB 8 | WT 9 | NTC 10 |
|---|---|---|---|---|---|---|---|---|---|---|---|---|
| HEX/Quasar | 34A | A | 13.3 | 29.6 | 26.6 | 33.5 | | | 31.7 | 10.6 | 25.1 | |
| HEX/Quasar | 34C | B | 23.1 | 13.2 | 19.7 | 28.4 | | | 31.8 | 10.5 | 26.4 | |
| FAM/Quasar | 34T | C | 22.5 | 20.2 | 10.8 | 28.5 | | 34.3 | 25.7 | 9.2 | 21.1 | |
| HEX/Quasar | 35A | D | 25.3 | 13.8 | 24.5 | 12.9 | 28.4 | 27.9 | 31.1 | 10.4 | 26.8 | |
| HEX/Quasar | 35C | E | 29.4 | 30.5 | | | 19.6 | 11.6 | 18.2 | 29.9 | 10.4 | 26.2 |
| FAM/Quasar | 35T | F | 27.2 | 14.1 | 25.3 | 22.0 | | 13.2 | 27.6 | 8.6 | 26.5 | |
| FAM/Quasar | 38A | G | 31.7 | 32.6 | 32.6 | 32.0 | 23.5 | | 10.4 | 9.4 | 22.0 | 26.0 |
| FAM/HEX/ Quasar | All Multiplex | H | 18.3/ 11 | 13.4/ 10 | 12.3/ 18.6 | 13.5/ 8.6 | 22.2/ 11.8 | 12.7/ 15.3 | 13.6/ 33 | 29.6/ 10.5 | 25.4/ 22.1 | |

When a plasmid containing a triple insert of 2 KRAS mutations (35C & 38A) and one ACTB (i.e., 35C/38A/ACTB plasmid), was used as calibrators (i.e. standard curves) to calculate strand numbers for all other mutations, data showing the following was obtained:
 a) Less than 0.05% cross reactivity between the multiplex KRAS mutant oligonucleotide mixes and wild-type KRAS.
 b) 35C standard curve calibrator can be used to quantify the HEX-reporting mutants (35A, 35C, 34A, 34C) and, similarly, that the 38A standard curve calibrator can be used to quantify the FAM-reporting mutants (38A, 34T, 35T).
 c) The assay can be used for both detection (i.e. screening for mutations) and quantification of KRAS mutants with minimal cross-reactivity with wild-type.
 d) The sensitivity of the assay is approximately a single-copy per reaction.

Additionally, using the multiplex KRAS mutant assay designs for screening previously sequenced tissue samples by assigning the HEX signal (35C calibrator) as an indicator for the presence of the 35A, 35C, 34A, 34C mutations and the FAM signal (38A calibrator) as an indicator for the presence of the 38A, 34T, 35T mutations the following results were obtained:

Test of tissue and stool samples with 3 color KRAS QuARTS assay

| Sample ID | Genotype by sequencing | Colon tissue histology | KRAS 35C Strands* | KRAS 38A Strands* | ACTB Strands (35C)** | ACTB Strands (38A)** | % mutation HEX | % mutation FAM | Call |
|---|---|---|---|---|---|---|---|---|---|
| | | | Tissue Samples | | | | | | |
| 054DAA | G34T | ADENOMA | — | 6,785 | 17,998 | 22,346 | 0% | 30% | Positive |
| 036DAA | G35A | CANCER | 641 | 1,061 | 4,890 | 5,953 | 13% | 18% | Positive |
| 029DAA | G34A | CANCER | 34,833 | 2,509 | 56,382 | 72,416 | 62% | 3% | Positive |
| 089DAA | G35A | ADENOMA | 126 | 180 | 1,821 | 2,098 | 7% | 9% | Positive |
| 056DAA | G35T | ADENOMA | 0 | 485 | 1,063 | 1,282 | 0% | 38% | Positive |
| 026DAA | G38A | CANCER | — | 29,200 | 41,166 | 52,430 | 0% | 56% | Positive |
| 019DAA | WT | normal colon | — | — | 42,028 | 51,976 | 0% | 0% | Negative |
| 008DAA | WT | normal colon | — | 3 | 39,535 | 48,897 | 0% | 0% | Negative |
| 092DAA | WT | normal colon | — | 16 | 81,065 | 100,809 | 0% | 0% | Negative |
| 017DAA | WT | normal colon | — | 32 | 113,608 | 149,212 | 0% | 0% | Negative |
| 013DAA | WT | normal colon | — | 50 | 99,401 | 130,064 | 0% | 0% | Negative |
| S1 | G35T | ADENOMA | 33 | 5,353 | 18,647 | 22,351 | 0% | 24% | Positive |
| S17 | G38A | CANCER | — | 5,227 | 9,971 | 11,816 | 0% | 44% | Positive |
| S40 | G34T | CANCER | — | 14,732 | 13,856 | 16,462 | 0% | 89% | Positive |
| S84 | WT | normal colon | — | 6 | 29,760 | 36,621 | 0% | 0% | Negative |
| S85 | WT | normal colon | — | 1 | 11,982 | 14,111 | 0% | 0% | Negative |
| S86 | WT | normal colon | — | 63 | 161,567 | 206,770 | 0% | 0% | Negative |
| S87 | WT | normal colon | — | — | 22,006 | 26,459 | 0% | 0% | Negative |
| | | | Stool Samples | | | | | | |
| Sample ID | Genotype by sequencing | Colon tissue histology | KRAS 35C Strands | KRAS 38A Strands | ACTB Strands (35C) | ACTB Strands (38A) | % mutation HEX | % mutation FAM | Call |
| S12 | 38G > A | CANCER | 4 | 15,845 | 48,028 | 36,827 | 0% | 33% | Positive |
| S11 | 34G > T | CANCER | — | 2,473 | 10,672 | 8,410 | 0% | 23% | Positive |
| S8 | 35G > A | CANCER | 1,156 | 1,379 | 173,401 | 129,130 | 1% | 1% | Positive |
| S9 | 35G > T | ADENOMA | 122 | 17,057 | 59,046 | 45,326 | 0% | 29% | Positive |
| S2 | 35G > T | CANCER | 44 | 8,079 | 72,221 | 55,335 | 0% | 11% | Positive |
| S7 | 38G > A | CANCER | 1 | 11,441 | 117,166 | 88,606 | 0% | 10% | Positive |
| S3 | 35G > T | CANCER | 2 | 956 | 12,573 | 9,921 | 0% | 8% | Positive |
| S21 | 35G > T | ADENOMA | 20 | 474 | 27,373 | 21,292 | 0% | 2% | Positive |

*Two plasmids, 35C/ACTB and 38A/ACTB, were used for generation of standard curves for HEX/Quasar and FAM/Quasar, respectively.
**ACTB Strands (35C) are calculated based on the ACTB/Quasar standard curve generated using the 35C/ACTB plasmid.
**ACTB Strands (38A) are calculated based on the ACTB/Quasar standard curve generated using the 38A/ACTB plasmid.

The data shows full agreement between QuARTS and sequencing. This indicates that the KRAS mutant QuARTS assay can be used on both stool DNA as well as tissue samples to screen for KRAS mutations.

What is claimed is:

1. A kit comprising:
   at least seven different primers that each comprise, at their 3' end, at least 12 contiguous nucleotides starting from the 3' end of a sequence selected from SEQ ID NOs: 1-7, wherein the primers are in one or more containers.

2. The kit of claim 1, wherein each primer is in a separate container.

3. The kit of claim 1, wherein the primers are each complementary to at least 16 nucleotides in the human KRAS gene.

4. The kit of claim 1, wherein the primers each comprise a sequence selected from SEQ ID NOS: 1-7.

5. The kit of claim 1, further comprising a reverse primer that hybridizes to the human KRAS gene.

6. The kit of claim 1, wherein the kit further comprises a thermostable polymerase.

7. The kit of claim 1, wherein the kit further comprises nucleotides.

8. The kit of claim 1, further comprising flap assay reagents that comprise a flap endonuclease, a FRET cassette that produces a fluorescent signal when cleaved, and at least seven different flap oligonucleotides.

9. The kit of claim 8, wherein the flap oligonucleotides each base pair with 10 to 14 contiguous nucleotides of the human KRAS gene.

10. The kit of claim 9, wherein the flap oligonucleotides each comprise at their 3' ends at least 11 contiguous nucleotides starting from the 3' end of a sequence as set forth in SEQ ID NOs: 11-17.

11. The kit of claim 1, wherein the kit comprises:
   a) amplification reagents comprising a thermostable polymerase, nucleotides, said at least seven different primers, and a reverse primer, wherein each of the seven different primers, in combination with said reverse primer, selectively amplifies a different allele of a KRAS gene, wherein the allele that is amplified is defined by a point mutation selected from 34A, 34C, 34T, 35A, 35C, 35T and 38A; and
   b) flap assay reagents comprising a flap endonuclease, a first FRET cassette that produces a fluorescent signal when cleaved, said at least seven different primers, and a corresponding set of at least seven different flap oligonucleotides that each comprise a nucleotide that base pairs with one of the point mutations.

12. The kit of claim 11, wherein the seven different flap oligonucleotides comprise at their 3' ends at least 11 contiguous nucleotides starting from the 3' end of a sequence as set forth in SEQ ID NOs: 11-17.

* * * * *

SEQUENCE LISTING

<160> NUMBER OF SEQ ID NOS: 30

<210> SEQ ID NO 1
<211> LENGTH: 21
<212> TYPE: DNA
<213> ORGANISM: Artificial sequence
<220> FEATURE:

<223> OTHER INFORMATION: Synthetic nucleic acid sequence

<400> SEQUENCE: 1
acttgtggta gttggagctc a                                              21

<210> SEQ ID NO 2
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 2
acttgtggta gttggagctc t                                              21

<210> SEQ ID NO 3
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 3
aacttgtggt agttggagat gc                                             22

<210> SEQ ID NO 4
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 4
cttgtggtag ttggagcca                                                 19

<210> SEQ ID NO 5
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 5
cttgtggtag ttggagcct                                                 19

<210> SEQ ID NO 6
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 6
tataaacttg tggtagttgg acctc                                          25

<210> SEQ ID NO 7
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 7
tggtagttgg agctggtaa                                                 19

```
<210> SEQ ID NO 8
<211> LENGTH: 22
<212> TYPE: DNA
<213> ORGANISM: Artificial sequence
<220> FEATURE:
<223> OTHER INFORMATION: Synthetic nucleic acid sequence

<400> SEQUENCE: 8
gattctgaat tagctgtatc gt                                              22

<210> SEQ ID NO 9
<211> LENGTH: 19
<212> TYPE: DNA
<213> ORGANISM: Artificial sequence
<220> FEATURE:
<223> OTHER INFORMATION: Synthetic nucleic acid sequence

<400> SEQUENCE: 9
ccatgaggct ggtgtaaag                                                  19

<210> SEQ ID NO 10
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 10
ctactgtgca cctacttaat acac                                            24

<210> SEQ ID NO 11
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 11
gcgcgtcctt ggcgtaggca                                                 20

<210> SEQ ID NO 12
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 12
ccacggacgc tggcgtaggc a                                               21

<210> SEQ ID NO 13
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 13
ccacggacga tggcgtaggc a                                               21

<210> SEQ ID NO 14
<211> LENGTH: 20
<212> TYPE: DNA
<213> ORGANISM: Artificial sequence
<220> FEATURE:
<223> OTHER INFORMATION: Synthetic nucleic acid sequence
```

```
<400> SEQUENCE: 14
gcgcgtccac gtaggcaaga                                           20

<210> SEQ ID NO 15
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 15
gcgcgtcctg tggcgtaggc                                           20

<210> SEQ ID NO 16
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 16
ccacggacgc gtggcgtagg c                                         21

<210> SEQ ID NO 17
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 17
ccacggacga gtggcgtagg c                                         21

<210> SEQ ID NO 18
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 18
cgccgagggc ggccttggag                                           20

<210> SEQ ID NO 19
<211> LENGTH: 29
<212> TYPE: DNA
<213> ORGANISM: Artificial sequence
<220> FEATURE:
<223> OTHER INFORMATION: Synthetic nucleic acid sequence

<400> SEQUENCE: 19
agccggtttt ccggctgaga cgtccgtgg                                 29

<210> SEQ ID NO 20
<211> LENGTH: 28
<212> TYPE: DNA
<213> ORGANISM: Artificial sequence
<220> FEATURE:
<223> OTHER INFORMATION: Synthetic nucleic acid sequence

<400> SEQUENCE: 20
agccggtttt ccggctgaga ggacgcgc                                  28

<210> SEQ ID NO 21
<211> LENGTH: 28
```

```
<212> TYPE: DNA
<213> ORGANISM: Artificial sequence
<220> FEATURE:
<223> OTHER INFORMATION: Synthetic nucleic acid sequence

<400> SEQUENCE: 21
agccggtttt ccggctgaga cctcggcg                                              28

<210> SEQ ID NO 22
<211> LENGTH: 72
<212> TYPE: DNA
<213> ORGANISM: Homo sapiens

<400> SEQUENCE: 22
tataaacttg tggtagttgg agctagtggc gtaggcaaga gtgccttgac gatacagcta          60
attcagaatc at                                                              72

<210> SEQ ID NO 23
<211> LENGTH: 72
<212> TYPE: DNA
<213> ORGANISM: Homo sapiens

<400> SEQUENCE: 23
tataaacttg tggtagttgg agcttgtggc gtaggcaaga gtgccttgac gatacagcta          60
attcagaatc at                                                              72

<210> SEQ ID NO 24
<211> LENGTH: 72
<212> TYPE: DNA
<213> ORGANISM: Homo sapiens

<400> SEQUENCE: 24
tataaacttg tggtagttgg agctcgtggc gtaggcaaga gtgccttgac gatacagcta          60
attcagaatc at                                                              72

<210> SEQ ID NO 25
<211> LENGTH: 72
<212> TYPE: DNA
<213> ORGANISM: Homo sapiens

<400> SEQUENCE: 25
tataaacttg tggtagttgg agctgatggc gtaggcaaga gtgccttgac gatacagcta          60
attcagaatc at                                                              72

<210> SEQ ID NO 26
<211> LENGTH: 72
<212> TYPE: DNA
<213> ORGANISM: Homo sapiens

<400> SEQUENCE: 26
tataaacttg tggtagttgg agctgttggc gtaggcaaga gtgccttgac gatacagcta          60
attcagaatc at                                                              72

<210> SEQ ID NO 27
<211> LENGTH: 72
<212> TYPE: DNA
<213> ORGANISM: Homo sapiens

<400> SEQUENCE: 27
tataaacttg tggtagttgg agctgctggc gtaggcaaga gtgccttgac gatacagcta          60
```

```
<210> SEQ ID NO 28
<211> LENGTH: 72
<212> TYPE: DNA
<213> ORGANISM: Homo sapiens

<400> SEQUENCE: 28
tataaacttg tggtagttgg agctggtgac gtaggcaaga gtgccttgac gatacagcta    60
attcagaatc at                                                        72

<210> SEQ ID NO 29
<211> LENGTH: 71
<212> TYPE: DNA
<213> ORGANISM: Homo sapiens

<400> SEQUENCE: 29
ctcgtgtgac aaggccatga ggctggtgta aagcggcctt ggagtgtgta ttaagtaggt    60
gcacagtagg t                                                         71

<210> SEQ ID NO 30
<211> LENGTH: 72
<212> TYPE: DNA
<213> ORGANISM: Homo sapiens

<400> SEQUENCE: 30
tataaacttg tggtagttgg agctggtggc gtaggcaaga gtgccttgac gatacagcta    60
attcagaatc at                                                        72
```